(12) United States Patent
Ashman et al.

(10) Patent No.: US 8,515,686 B2
(45) Date of Patent: Aug. 20, 2013

(54) DETECTION AND QUANTIFICATION OF POLYPEPTIDES USING MASS SPECTROMETRY

(75) Inventors: Keith Ashman, North Ryde (AU); Matthew McKay, North Ryde (AU); James Sherman, North Ryde (AU); Mark Molloy, North Ryde (AU)

(73) Assignee: Macquarie University, New South Wales (AU)

(*) Notice: Subject to any disclaimer, the term of this patent is extended or adjusted under 35 U.S.C. 154(b) by 677 days.

(21) Appl. No.: 11/922,690

(22) PCT Filed: Dec. 18, 2007

(86) PCT No.: PCT/AU2007/001951
§ 371 (c)(1),
(2), (4) Date: Aug. 13, 2010

(87) PCT Pub. No.: WO2008/074067
PCT Pub. Date: Jun. 26, 2008

(65) Prior Publication Data
US 2010/0299081 A1    Nov. 25, 2010

Related U.S. Application Data

(60) Provisional application No. 60/885,373, filed on Jan. 17, 2007.

(30) Foreign Application Priority Data

Dec. 18, 2006    (AU) ................................ 2006907017

(51) Int. Cl.
*G01N 31/00* (2006.01)
(52) U.S. Cl.
USPC ............................................. 702/27; 702/28

(58) Field of Classification Search
USPC .................................. 702/19, 20, 23, 27, 28
See application file for complete search history.

(56) References Cited

U.S. PATENT DOCUMENTS 7,069,152 B2    6/2006    Skillings
2004/0121477 A1*    6/2004    Thompson et al. ............. 436/86

(Continued)

FOREIGN PATENT DOCUMENTS

EP    1047107 B1    10/2006
WO    WO 01/57519 A2    8/2001

(Continued)

OTHER PUBLICATIONS

Anderson, et al., "Quantitative Mass Spectrometric Multiple Reaction Monitoring Assays for Major Plasma Proteins," Molecular & Cellular Proteomics, (Dec. 6, 2005), pp. 573-588, vol. 5.4.
Cox, et at, "Multiple Reaction Monitoring as a Method for Identifying Protein Posttranslational Modifications," Journal of Biomolecular Techniques, (Jun. 2005), pp. 83-90, vol. 16, Issue 2.

(Continued)

*Primary Examiner* — Sujoy Kundu
*Assistant Examiner* — Harun Chowdhury
(74) *Attorney, Agent, or Firm* — Richard F. Trecartin; Morgan, Lewis & Bockius LLP

(57) ABSTRACT

The invention relates to the detection and quantification of polypeptides using mass spectrometry. Specifically, the invention provides a method for testing whether a target polypeptide is present in a sample of a set of polypeptides, a method for deriving a value for distinguishing polypeptides of a set of polypeptides from each other, a database containing values for distinguishing each polypeptide of a set of polypeptides from each other, and an apparatus for configuring a mass scan of a mass spectrometer to test whether a target polypeptide of a set of polypeptides is present in a sample of the set.

10 Claims, 21 Drawing Sheets

(56) References Cited

U.S. PATENT DOCUMENTS

2006/0009915 A1* 1/2006 Goodlett .................... 702/19
2006/0022129 A1* 2/2006 Shchepinov et al. ......... 250/282
2007/0090287 A1* 4/2007 Foote et al. ................. 250/292

FOREIGN PATENT DOCUMENTS

WO    WO 02/052259 A1    7/2002
WO    WO 02/095419 A2   11/2002

OTHER PUBLICATIONS

Jacobs, et al., "Utilizing Human Blood Plasma for Proteomic Biomarker Discovery," Journal of Proteome Research, (2005), pp. A-M.

Unwin, etal., "Multiple Reaction Monitoring to Identify Sites of Protein Phosphorylation With High Sensitivity," Molecular & Cellular Proteomics, (May 27, 2005), pp. 1134-1144, vol. 4.8.

* cited by examiner

DETECTION AND QUANTIFICATION OF POLYPEPTIDES USING MASS SPECTROMETRY

FIELD OF THE INVENTION

The invention relates to the detection and quantification of polypeptides using mass spectrometry.

BACKGROUND OF THE INVENTION

Mass spectrometry is commonly used in protein chemistry and proteomics to identify polypeptides and to determine their relative abundance. Mass spectrometry is also used to test a sample for the presence of a known polypeptide and the relative abundance of it.

The application generally requires the following steps: (1) introduce a sample into a mass spectrometer (herein "MS"); (2) utilise the MS to scan the sample; and (3) compare the data acquired from the scan against a database containing information acquired from previous MS experiments, or from a database containing predicted sample mass information to test for the presence and/or abundance of the known ("target") polypeptide in the sample.

Generally speaking, there are four modes by which a MS can be configured to scan and acquire data.

A first mode is full scan acquisition. In this mode, the scan acquires information on the mass/charge ratio (herein "m/z") of all polypeptides introduced into the MS. This is exemplified by the method known as peptide mass fingerprinting (PMF). In the case of a low complexity mixture, such as a purified polypeptide, PMF is often sufficient to identify the polypeptide analyte by matching observed m/z values against expected theoretical values. However, a problem arises where the sample is a complex mixture of polypeptides such as serum or a cell/tissue lysate; as the m/z's of many polypeptides are detected in the scan, making it very difficult to identify a target polypeptide. This is particularly the case where the target polypeptide has a low relative abundance in the sample. Also the mass range over which the m/z of polypeptides can be accurately determined is limited leading to overlapping signals in complex samples. Suppression effects in the ionization process results in the loss of signal from some polypeptides.

To improve identification specificity, a second mode of MS known as tandem MS (MS/MS) can be conducted. In this case, an m/z ion obtained from a MS scan is selected and fragmented for example, by collision-induced dissociation (CID) with a gas. This produces a series of fragment ions that originated from a precursor ion. Coupling the m/z of the precursor ion with the m/z of the fragment ions increases identification specificity when the masses are compared against a sequence database as described above. Nonetheless, for complex samples this approach is limited to identifying approximately 5-15% of the spectra generated and amongst this are many false-positive identifications. [Keller, A., Nesvizhskii, A. I., Kolker, E., Aebersold, R. (2002) Empirical statistical model to estimate the accuracy of peptide identifications made by MS/MS and database search. Anal. Chem. 74, 5383-5392. Nielsen, M. L., Savitski, M. M., Zubarev, R. A. (2005) Improving polypeptide identification using complementary fragmentation techniques in Fourier transform mass spectrometry. Mol. Cell. Proteomics 4, 835-845.]

If the MS/MS data quality contains an ion series representative of each amino acid of the analyte polypeptide, the amino acid sequence can be readily determined from the spectra via de novo sequence analysis. However, in practice, data of this quality occurs at low frequency. To overcome the limitations of imperfect spectra the accepted approach is to utilize the imperfect MS/MS spectra as a signal and then filter through the database for those sequences containing the MS/MS signal. Two basic methods exist for this purpose, the first proposed by Yates and Eng is the cross-correlation method, and the second proposed by Mann is based on the related idea of sequence tag matching. The technical limitations of both these approaches and the larger methodologies that they have evolved into are that they ultimately assign a polypeptide identity and a concomitant P-value. The P-value is a measure of confidence that a human investigator would assign the same identity if manually inspecting (Nesvizhskii 2002 supra). Thus it is possible and even probable that spectra are generated by the MS that do not contain enough information to uniquely match them to a polypeptide sequence however they would still be scored well (false-positive). In net terms, these signal filtering techniques are unable to determine when an MS/MS spectra lacks sufficient information content to determine an identity, thus they are incapable of returning a negative result but instead leave it to the user to choose a cut off value of confidence in the database search result.

A third mode is single ion monitoring (SIM). SIM scans are performed by configuring a MS to scan for polypeptides having a selected m/z. While polypeptides not having the selected m/z are excluded from detection, SIM scans detect all polypeptides having a m/z that is indistinguishable from the target polypeptide m/z. Accordingly, where the sample contains polypeptides having a m/z that is the same as the target polypeptide (again, this is common where the sample includes a complex mixture of polypeptides), multiple peaks are presented in a plot of relative intensity against m/z, thereby confounding polypeptide identity. Again, the sensitivity of this mode becomes an issue where the target polypeptide has a low relative abundance relative to other polypeptides having the same m/z.

The fourth mode is selected reaction monitoring (SRM). In this mode, the MS is configured to scan for the presence of both a precursor m/z ion (typically known as a Q1 value) and a fragment ion (typically known as a Q3 value) that is generated when polypeptides having a particular precursor m/z are fragmented (e.g. by CID). Typically, both the Q1 and Q3 value are determined from a database containing information acquired from either previous MS experiments, or theoretical calculations (MIDAS). The combination of Q1 and Q3 ion m/z that map to a given polypeptide, enables the monitoring of polypeptide abundance.

A limitation of the SRM approach with complex samples is that many different combinations of polypeptides can occupy the same mass transmission window centred around Q1 and Q3 values, thus compromising the technique for polypeptide identification purposes. Therefore, unless a definitive MS scan can be conducted (or has been previously conducted) that contains information in addition to Q1 and Q3 values (such as obtained in a tandem MS scan) it is not possible to identify the analyte with any confidence using solely Q1 and Q3 values. This means that most if not all Q1, Q3 pairs for a given polypeptide will map to one or more other polypeptides, especially in the context of a complex mixture of polypeptides. For those polypeptides in a complex sample that are detectable, it is economically unattractive and experimentally cumbersome to perform MS experiments for every polypeptide to identify a fragment ion that will uniquely identify each polypeptide.

There is a need to be able to determine the presence and/or abundance of any given target polypeptide in a complex mixture of polypeptides, and especially those having low relative abundance.

SUMMARY OF THE INVENTION

The invention seeks to at least minimise or reduce one or more of the above limitations or problems and in certain embodiments provides a method for testing whether a target polypeptide is present in a sample of a set of polypeptides. The method includes the following steps:
a) providing a sample of a set of polypeptides to be tested for the presence of a target polypeptide;
b) selecting a database corresponding to the set of polypeptides having information stored therein that describes a characteristic of each polypeptide of the set;
c) interrogating the database to determine a value for the target polypeptide that can be used to configure a mass spectrometer to exclude the detection of polypeptides having a value that is not the same as the value determined for the target polypeptide, so that the target polypeptide may be selectively detected by the mass spectrometer;
d) utilizing the value determined for the target polypeptide to configure the mass spectrometer;
e) applying the sample of the set of polypeptides to the configured mass spectrometer; and
f) utilizing the configured mass spectrometer to test whether the target polypeptide is present in the sample of the set of polypeptides.

In other embodiments there is provided a method for deriving a value for distinguishing polypeptides of a set of polypeptides from each other. The method includes:
a) selecting a database having information representing amino acid sequences of substantially all polypeptides of a set of polypeptides stored therein;
b) utilizing each sequence to predict a mass/charge ratio for each polypeptide of the set of polypeptides obtainable when a pre-defined sample ionisation condition is applied to polypeptides of the set;
c) selecting sequences that represent polypeptides that have the same predicted mass/charge ratio;
d) predicting a mass of each fragment ion obtainable from polypeptides represented by each selected sequence when a pre-defined fragmentation condition is applied to each polypeptide represented by the selected sequences;
e) for each polypeptide represented by the selected sequences, identifying a predicted mass of at least one fragment ion that is different from the predicted masses of fragment ions of polypeptides represented by other selected sequences;
thereby deriving a value for each polypeptide of the set of polypeptides that distinguishes polypeptides of the set from each other.

In other embodiments there is provided a database containing values for distinguishing each polypeptide of a set of polypeptides from each other. The database is created according to the following steps:
a) selecting a first database having information representing amino acid sequences of substantially all polypeptides of a set of polypeptides stored therein;
b) utilizing each sequence to predict a mass/charge ratio for each polypeptide of the set of polypeptides obtainable when a pre-defined ionisation condition is applied to polypeptides of the set;
c) selecting sequences that represent polypeptides that have the same predicted mass/charge ratio;
d) predicting a mass of each fragment ion obtainable from polypeptides represented by each selected sequence when a pre-defined fragmentation condition is applied to each polypeptide represented by the selected sequences;
e) for each polypeptide represented by the selected sequences, identifying a predicted mass of at least one fragment ion that is different from the predicted masses of fragment ions of polypeptides represented by other selected sequences, to derive a value for each polypeptide of the set of polypeptides that distinguishes polypeptides of the set from each other;
f) storing each value so derived in a computer readable medium, thereby creating the database containing values for distinguishing each polypeptide of a set of polypeptides from each other.

An apparatus for configuring a mass scan of a mass spectrometer to test whether a target polypeptide of a set of polypeptides is present in a sample of the set including:
a) a processor having stored thereon an executable code for deriving a value for distinguishing a target polypeptide from other polypeptides of a set of polypeptides;
b) input means in communication with the processor for identifying the target polypeptide for which the value is to be derived by the executable code;
c) configuring means in communication with the processor for configuring a mass scan of a mass spectrometer according to the value derived by the executable code;
wherein in use, the executable code derives the value according to the following steps:
(i) utilizing information representing the amino acid sequences of the polypeptides of the set of polypeptides to predict a mass/charge ratio for each polypeptide obtainable when a pre-defined ionisation condition is applied to polypeptides of the set;
(ii) selecting sequences that represent polypeptides that have the same predicted mass/charge ratio as the target polypeptide;
(iii) predicting a mass of each fragment ion obtainable from polypeptides represented by each selected sequence when a pre-defined fragmentation condition is applied to each polypeptide represented by the selected sequences;
(iv) identifying a predicted mass of at least one fragment ion of the target polypeptide that is different from the predicted masses of fragment ions of polypeptides represented by the selected sequences;
thereby deriving a value for distinguishing the target polypeptide from other polypeptides of a set of polypeptides.

DETAILED DESCRIPTION OF THE EMBODIMENTS

Figure 1:
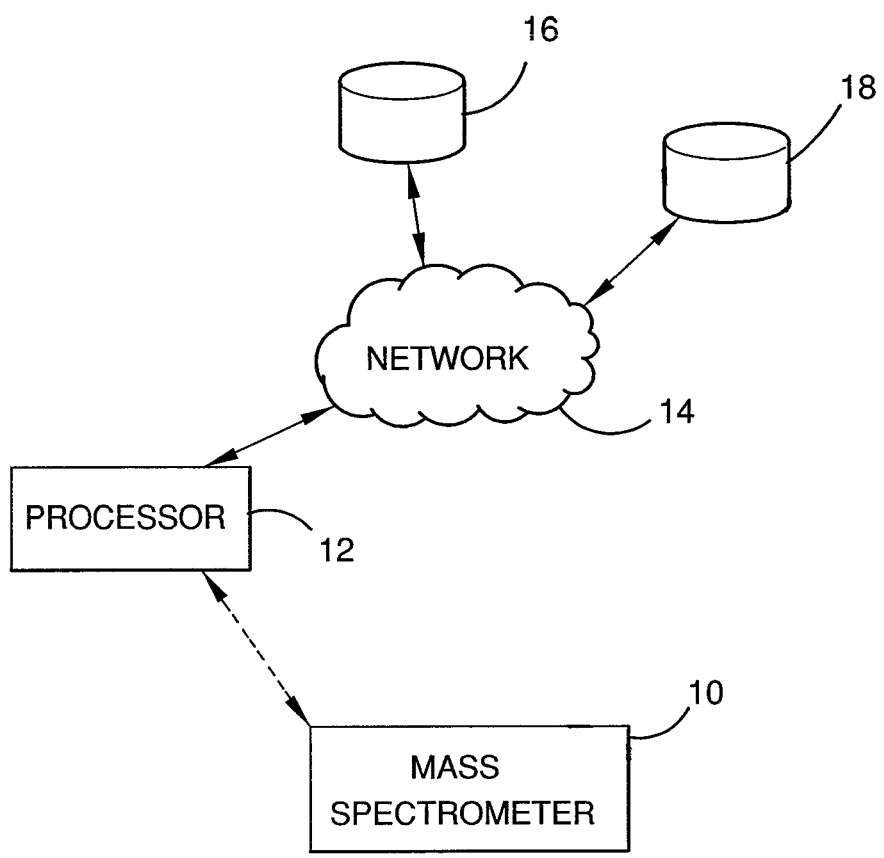
FIG. 1 shows a system that may be used to implement the described methods.

The inventors have developed a new methodology for testing for the presence and/or abundance of a target polypeptide in a sample. The new methodology is referred to herein as unique selected reaction monitoring (USRM). The key steps of the methodology involve utilizing a database to determine a value that uniquely identifies a target polypeptide and that distinguishes it from other polypeptides in a given set of polypeptides in a given experimental context. The determined value is then used to configure a mass spectrometer (herein "MS") so that the MS scans a field defined by the value at which the target polypeptide, if present in the sample, is expected to be detected. The determined value is referred to herein as a unique mass descriptor (UMD).

This methodology is contrary to the methods conventionally used before the invention which have involved an opposite approach, i.e. acquiring scanned data from a MS experiment and then comparing the acquired data with a database to identify the presence and/or abundance of a target polypeptide in a sample.

Thus in certain embodiments there is provided a method for testing whether a target polypeptide is present in a sample of a set of polypeptides. The method includes the following steps:

a) providing a sample of a set of polypeptides to be tested for the presence of a target polypeptide;

b) selecting a database corresponding to the set of polypeptides having information stored therein that describes a characteristic of each polypeptide of the set;

c) interrogating the database to determine a value for the target polypeptide that can be used to configure a MS to exclude the detection of polypeptides having a value that is not the same as the value determined for the target polypeptide, so that the target polypeptide may be selectively detected by the MS;

d) utilizing the value determined for the target polypeptide to configure the MS;

e) applying the sample of the set of polypeptides to the configured MS; and f) utilizing the configured MS to test whether the target polypeptide is present in the sample of the set of polypeptides.

As described herein, a first step in these embodiments involves providing a sample of a set of polypeptides to be tested for the presence of a target polypeptide.

The "set of polypeptides" referred to herein (otherwise known as a "composition", "collection", "combination" "collocation" or "array" of polypeptides) may be "a proteome". A "proteome" is generally understood as meaning the complete set of polypeptides from the information encoded on a genome as expressed and/or modified by a cell, tissue, or organism at a given sampling time. One example is serum/plasma. Other examples include entire organisms such as bacteria, yeast, fungi, invertebrates. Also, components of organisms such as tissues or cells produced in culture. Another example could include combinations of organisms such bacteria and bacteriophages. Other examples include biological fluids such as tears, cerebro spinal fluid (CSF), saliva, urine. It could also include purified fractions of any of the above.

It will also be understood that the "set of polypeptides" referred to herein may represent other than the whole of a proteome. For example it may represent part of a proteome such as a mitochondrion or plasma membrane. The part of the proteome may be obtained by any technique for fractionating, separating, dividing and/or other chromatographic methodologies. One example is fractionated human serum, for example, serum that has been fractionated according to molecular weight or immunodepleted of particular polypeptides.

Further, the "set of polypeptides" may be polypeptides synthesised by gene expression occurring naturally in a cell, whether under normal physiological or pathological conditions. These polypeptides may be secreted or obtained by lysing and extracting them from a cell.

Alternatively, "the set of polypeptides" may be polypeptides that have been synthesised either chemically or otherwise, for example by recombinant DNA technology. In these embodiments, the "set of polypeptides" may be representative of those that are synthesised by gene expression occurring naturally in a cell. However, they may be different in the sense that they may or may not have been subjected to post-translational modifications that are normally observed when expressed in the cell of origin.

Alternatively, the "set of polypeptides" may be polypeptides that are not representative of any naturally occurring combination of polypeptides. One example is where polypeptides representative of one origin or derivation (for example, in the sense of being synthesised by gene expression occurring naturally in a given cell) are mixed with polypeptides of another. Another example is where polypeptides of one origin or derivation are mixed with other polypeptides of the same or different origin or derivation, the latter being distinguished by having been modified or altered, for example by chemical or metabolic labelling.

Further still, the "set of polypeptides" may consist of polypeptides that are not naturally occurring. One example consists of polypeptides that are represented in the form of fusion polypeptides in an expression library, for example a phage library. Another example are polypeptides that are formed by gene shuffling or other mutagenic techniques. A further example is polypeptides that contain additional domains useful or other purposes such as a His-tag or being linked to green fluorescent protein.

One example of a "set of polypeptides" is polypeptides that are observed in response to an artificial stimulus. In one example, the "set of polypeptides" is observed in response to exposing a cell, tissue, organ, or lysates of any of these, or serum, to a chemical agent such as a pharmaceutical or veterinarian chemical principle, pesticide, insecticide, herbicide or other compound that is useful for, or to be tested for providing a desired or undesired biological effect.

It will be understood in certain embodiments, a "polypeptide" may be a peptide, generally unrestricted by molecular weight. The polypeptide or peptide may represent what is commonly recognised as a "mature polypeptide" (i.e. one that has been subjected to post-translational modification), a fragment or domain of a mature polypeptide whether functional or otherwise, or pro or pre-pro isoforms of mature polypeptides, again, all of which may be naturally occurring or not.

The "sample" of the set of polypeptides may be obtained from any source, depending on the purpose of the assay. For example, if the purpose is to assay for the presence or abundance of a polypeptide in human serum, the sample of serum is from a human and ultimately directly introduced into the MS, or otherwise subjected to sample processing, for example to dilute, fractionate or modify particular polypeptides in the sample, or to add further molecules, for example, internal standards, labels or labelled molecules to the sample.

Examples of samples include those obtained from animal, plant, bacterial, viral and fungal organisms.

The target polypeptide may be any polypeptide, the presence of which is to be tested in a sample. Additionally or alternative, the abundance of a target polypeptide may be measured. Accordingly, in one embodiment there is provided a method for testing the relative abundance of a target polypeptide in a sample of a set of polypeptides. The method typically includes steps a) to f) described above.

In a second step the process involves selecting a database corresponding to the set of polypeptides that has information stored in it that describes a characteristic of each polypeptide of the set.

The database utilized in the second step may be selected according to the nature of the information contained within it and hence the nature of the characteristic described by it. In one example, the database contains the amino acid sequences of the set of polypeptides. Such a database is referred to herein as a "polypeptide database". The amino acid sequences may have been derived from previous "wet experiments" (i.e. experiments that have not been performed in silico). Alternatively, they may have been predicted from considering the open reading frame of a nucleotide sequence of a nucleic acid. In some embodiments, the polypeptide database consists of both predicted sequences and sequence derived from MS or other experiments. These databases may also contain information of polypeptide modifications such as phosphorylation and/or glycosylation. It will be recognised that the database may change over time as additional information from experiments is added. Examples of polypeptide databases include SWISS-PROT, PIR, Uni-Prot, PRF, NCBI.

In other embodiments, the database contains the nucleotide sequence of nucleic acids that encode the set of polypeptides. Such a database is referred to herein as a "nucleic acid database" The nucleotide sequences may have been derived from sequencing nucleic acid molecules. Alternatively, they may have been derived in silico. In these embodiments, the nucleotide sequences are used to predict the amino acid sequences corresponding to the set of polypeptides. Examples of nucleic acid databases include TrEMBL, EMBL-Bank, Ensembl.

In some embodiments the database that is selected is both a nucleic acid and a polypeptide database. One example is IPI (International Polypeptide Index), Celera Discovery Systems.

In the above embodiments, the characteristic of the polypeptides described by the information is amino acid sequence or nucleotide sequence. However, it will be understood that polypeptide or nucleic acid database may not contain these sequences. More specifically, in some embodiments, the polypeptide or nucleic acid database may contain integers or values that uniquely describe each of the amino acid and nucleotide sequences of the polypeptides or nucleic acids contained in the polypeptide and nucleic acid databases respectively.

In other embodiments, the characteristic of the polypeptides described by the information is not amino acid sequence or nucleotide sequence, but rather another characteristic that uniquely describes each polypeptide of the set. Whether a particular characteristic is suitable for this purpose depends in part on the complexity of the set of polypeptides. For example, where there are relatively few polypeptides, each having a relatively common abundance, the characteristic might be the molecular weight or isoelectric point.

Another characteristic contained in the database might be related to a functional activity. For example where the database corresponds to a library of enzymes and the information describes the specific activity of each enzyme, this characteristic may be used.

According to a second step of the method, the database is selected that corresponds to the particular set of polypeptides that is the subject of the investigation. It will be understood that a database corresponding to the set of polypeptides is one which contains information on the set of polypeptides anticipated in the sample. It will be understood that the database does not need to correspond exactly to the set of polypeptides in the sense of it containing information on nothing more than the polypeptides in the sample.

To elaborate further on the above, in one example the sample of set of polypeptides may consist of all polypeptides found in a human hepatocyte. The database corresponding to this set of polypeptides need not be limited to information on the set of polypeptides of the sample. It may and frequently will have information on other polypeptides that may not be expressed in the hepatocyte. Thus in this example, the database corresponding to the set of polypeptides maybe a polypeptide database representing all polypeptides predicted to be expressed by the human genome.

In certain embodiments, the database contains information on all of the polypeptides anticipated in the sample. However, it is not necessary for the database to contain information on all of the polypeptides anticipated in the sample. For example, the method works where the database contains information on polypeptides anticipated in the sample that have the same or similar m/z as the target polypeptide but does not contain information on other polypeptides anticipated in the sample having a different m/z as the target. In this sense, the database may contain information on "substantially all" polypeptides of a set of polypeptides stored therein.

In a third step the method involves interrogating the selected database. This is done for the purpose of determining or calculating a value or set of values for the target polypeptide that can be used to configure a MS. The value must be sufficient to exclude the detection of polypeptides having a value that is not the same as the value determined for the target polypeptide. In this way, the target polypeptide may be selectively detected by the MS.

The value that is determined must be one that is capable of being used to configure a MS. A MS may be configured for a particular scan and data acquisition in a number of ways, including full scan or tandem MS acquisition, single ion monitoring and selected reaction monitoring as described above. The choice of scan and configuration depends largely on the type of MS that is used. For example where the sample has low complexity, a single quadrupole MS, ion trap MS or time of flight MS may be used, and the value that is determined may be m/z, or a value representing this parameter. Where tandem MS is used for more complex samples, the value that is determined may be the polypeptide precursor m/z in addition to one or more fragment ion m/z such as but not limited to a, b, c, x, y, z ions or a value representing these parameters.

In certain embodiments the value for the target polypeptide is determined by determining a value for all polypeptides represented in the selected database. In other embodiments, the value for the target polypeptide is determined by determining the value for only a portion of the polypeptides represented in the selected database, for example, only those polypeptides having a molecular weight that is the same as the molecular weight of the target polypeptide.

The value for the target polypeptide may be determined by manually interrogating the database. Alternatively, the value may be determined using software. An example of the latter is discussed in the embodiments described further below.

In a fourth step the method involves utilizing the value determined for the target polypeptide to configure the MS.

In one embodiment, the value that is determined is a combination of the m/z of a precursor ion and one or more fragment ions derived from it and the MS is configured to scan for this combination.

In the remaining steps of the method, the sample of the set of polypeptides is applied to the configured MS and the configured MS is used to test whether the target polypeptide is present in the sample of the set of polypeptides. These steps are further exemplified in the examples set out below.

One key advantage of the process is that it enables one to validate the existence of polypeptides predicted from genome data. For example a particular predicted polypeptide can be selected as a target polypeptide, its unique value in the context of other polypeptides predicted from the genome identified and a mass spectrometer configured to scan a sample of polypeptides expressed from the genome. The detection of a signal corresponding to the pre-determined values would indicate the presence of a previously hypothetical polypeptide within that proteome A further advantage is that a target polypeptide can be detected within some proteomes with certainty without the need to pre-isolate or enrich for the target polypeptide. For example, a recombinant polypeptide expressed in cells may be detected by applying the entire sample to a configured MS.

In other embodiments there is provided a method for deriving a value for distinguishing polypeptides of a set of polypeptides from each other. The method includes:

a) selecting a database having information representing amino acid sequences of substantially all polypeptides of a set of polypeptides stored therein;
b) utilizing each sequence to predict a mass/charge ratio for each polypeptide of the set of polypeptides obtainable when a pre-defined ionisation condition is applied to polypeptides of the set;
c) selecting sequences that represent polypeptides that have the same predicted mass/charge ratio;
d) predicting a mass of each fragment ion obtainable from polypeptides represented by each selected sequence when a pre-defined fragmentation condition is applied to each polypeptide represented by the selected sequences;
e) for each polypeptide represented by the selected sequences, identifying a predicted mass of at least one fragment ion that is different from the predicted masses of fragment ions of polypeptides represented other selected sequences;

thereby deriving a value for each polypeptide of the set of polypeptides that distinguishes polypeptides of the set from each other.

In one embodiment, step b) involves utilizing each sequence to predict a mass/charge ratio for each polypeptide, of the set of polypeptides obtainable when a pre-defined ionisation condition and sample condition, such as sample protease digestion, for example trypsinization is applied to polypeptides of the set;

In one embodiment, a value for each polypeptide of the set of polypeptides that distinguishes polypeptides of the set from each other is obtained with completion of step c). In this embodiment, it is not necessary to proceed to step d) and further steps.

In another embodiment, after step c), the method includes the step of determining whether a value for each polypeptide of the set of polypeptides that distinguishes polypeptides of the set from each other is obtained with completion of step c). In the circumstances that a value has not been determined, a decision is made to proceed with following steps d) and e) to determine the value.

In one embodiment, in step e., a combination of predicted m/z values of fragment ions for each polypeptide represented by the selected sequences is identified that is different from the combinations of the predicted masses of fragment ions of polypeptides represented by other selected sequences. For example, the combination may include the predicted m/z of at least 2 fragment ions.

Advantageously, it has been found that it is possible to assign a value that specifically identifies and thereby distinguishes each polypeptide from others of a complex proteome such as the human proteome based on the predicted m/z of a precursor polypeptide and at least 2 fragment ions. This was unanticipated at the time of the invention. Indeed, prior to the invention, it was simply not known whether every polypeptide of a proteome could be uniquely identified by reference to a precursor ion m/z and fragment ion m/z.

Further, in many cases and especially the example of serum, the technology required to detect polypeptides that have a low relative abundance by MS experiments was not available prior to the invention. For those polypeptides having a higher relative abundance, it was considered prior to the invention to be not economically feasible to perform MS experiments for every polypeptide to identify a fragment ion that uniquely identifies each polypeptide.

In other embodiments there is provided a database containing values for distinguishing each polypeptide of a set of polypeptides from each other. The database is created according to the following steps:

a) selecting a first database having information representing amino acid sequences of substantially all polypeptides of a set of polypeptides stored therein;
b) utilizing each sequence to predict a mass/charge ratio for each polypeptide of the set of polypeptides obtainable when a pre-defined ionisation condition is applied to polypeptides of the set;
c) selecting sequences that represent polypeptides that have the same predicted mass/charge ratio;
d) predicting a mass of each fragment ion obtainable from polypeptides represented by each selected sequence when a pre-defined fragmentation condition is applied to each polypeptide represented by the selected sequences;
e) for each polypeptide represented by the selected sequences, identifying a predicted mass of at least one fragment ion that is different from the predicted masses of fragment ions of polypeptides represented by other selected sequences, to derive a value for each polypeptide of the set of polypeptides that distinguishes polypeptides of the set from each other;
f) storing each value so derived in a computer readable medium, thereby creating the database containing values for distinguishing each polypeptide of a set of polypeptides from each other.

In other embodiments there is provided an apparatus for configuring a mass scan of a mass spectrometer to test whether a target polypeptide of a set of polypeptides is present in a sample of the set including:
a) a processor having stored thereon an executable code for deriving a value for distinguishing a target polypeptide from other polypeptides of a set of polypeptides;
b) input means in communication with the processor for identifying the target polypeptide for which the value is to be derived by the executable code;
c) configuring means in communication with the processor for configuring a mass scan of a mass spectrometer according to the value derived by the executable code;
wherein in use, the executable code derives the value according to the following steps:
(i) utilizing information representing the amino acid sequences of the polypeptides of the set of polypeptides to predict a mass/charge ratio for each polypeptide obtainable when a pre-defined ionisation condition is applied to polypeptides of the set;
(ii) selecting sequences that represent polypeptides that have the same predicted mass/charge ratio as the target polypeptide;
(iii) predicting a mass of each fragment ion obtainable from polypeptides represented by each selected sequence when a pre-defined fragmentation condition is applied to each polypeptide represented by the selected sequences;
(iv) identifying a predicted mass of at least one fragment ion of the target polypeptide that is different from the predicted masses of fragment ions of polypeptides represented by the selected sequences;
thereby deriving a value for distinguishing the target polypeptide from other polypeptides of a set of polypeptides.

In certain embodiments, the value for the target polypeptide is a function of the m/z of the target polypeptide and the m/z of at least one fragment thereof. In other embodiments, the value is a function of the m/z of the target polypeptide and the m/z of at least two fragments thereof.

FIG. 1 shows a system that may be used to implement the described methods. Mass spectrometer 10 is used to analyse samples. Parameters for the analysis may be input directly into the mass spectrometer 10 by a user or by providing a work file to the mass spectrometer, for example on a storage disk. Alternatively, the parameters may be transferred electronically from a processor 12.

The processor 12 may be used to execute software in accordance with the methods described herein. As described below, the software running on the processor 12 may be used to determine one or more descriptors that uniquely characterise a target material (such as a specified protein) in a selected set. The descriptors are provided to the mass spectrometer 10 in order to scan for the target material.

The processor 12 is typically in data communication with a network 14, which may be the Internet. The network 14 provides access to other processors and a plurality of databases 16, 18, which may include public repositories of information such as the Human Proteome Organisation Plasma Proteome Project. Data stored in databases 16, 18 may be used as inputs to the methods executed by the processor 12.

The software running on the processor 12 may be stored on a computer-readable medium such as a CD and be loaded onto the processor 12 for execution. A computer-readable medium having software or a computer program recorded on it is a computer program product. The use of the computer program product with the processor 12 effects an apparatus for implementing the methods described herein.

Figure 2:
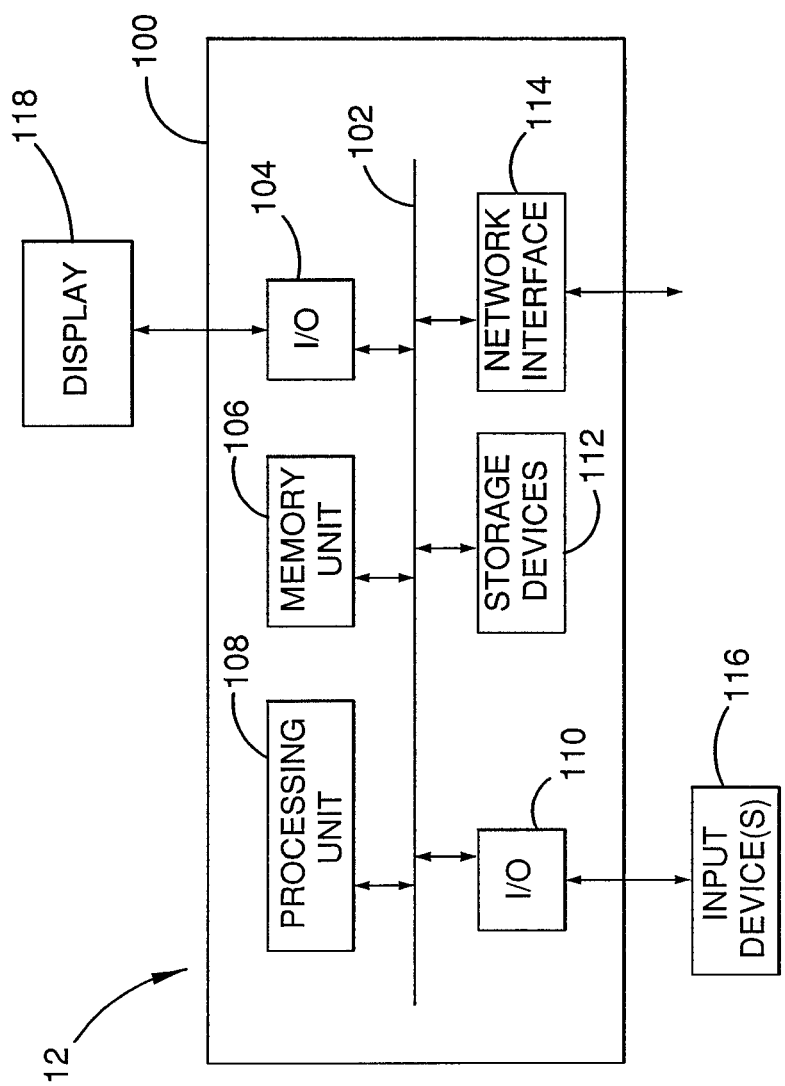
FIG. 2 shows schematically a configuration of the processor 12.

FIG. 2 shows schematically a configuration of the processor 12. Input devices 116 such as a keyboard and mouse are provided for a user to enter information and instructions into the processor 116. Display 118 is provided to display information to the user. Typically the processor module 100 includes at least one processing unit 108 and a memory unit 106 that includes random-access memory (RAM) and read-only memory (ROM). The module 100 includes an input/output (I/O) unit 104 to control communication with the display 118, and an I/O unit 110 to enable communication with the input devices 116.

The processor 12 also includes a network interface 114 to permit data communication with a network. The interface 114 may, for example, be an Ethernet™ card or a wireless connection such as Bluetooth™. The interface 114 enables communication via the network 14, possibly via intermediate devices or local networks.

The processor module 100 also typically includes one or more storage devices 112, for example a hard disk drive or an optical disk drive to read CDs or DVDs. Various portable machine-readable memory devices may be used to enter data and computer code into the processor 12. Data and computer code may also be transmitted to the processor 12 via the network interface 114 (for example downloaded over the Internet).

The components within the module 100 typically communicate via a bus 102.

EXAMPLES

Example 1

Figure 3:
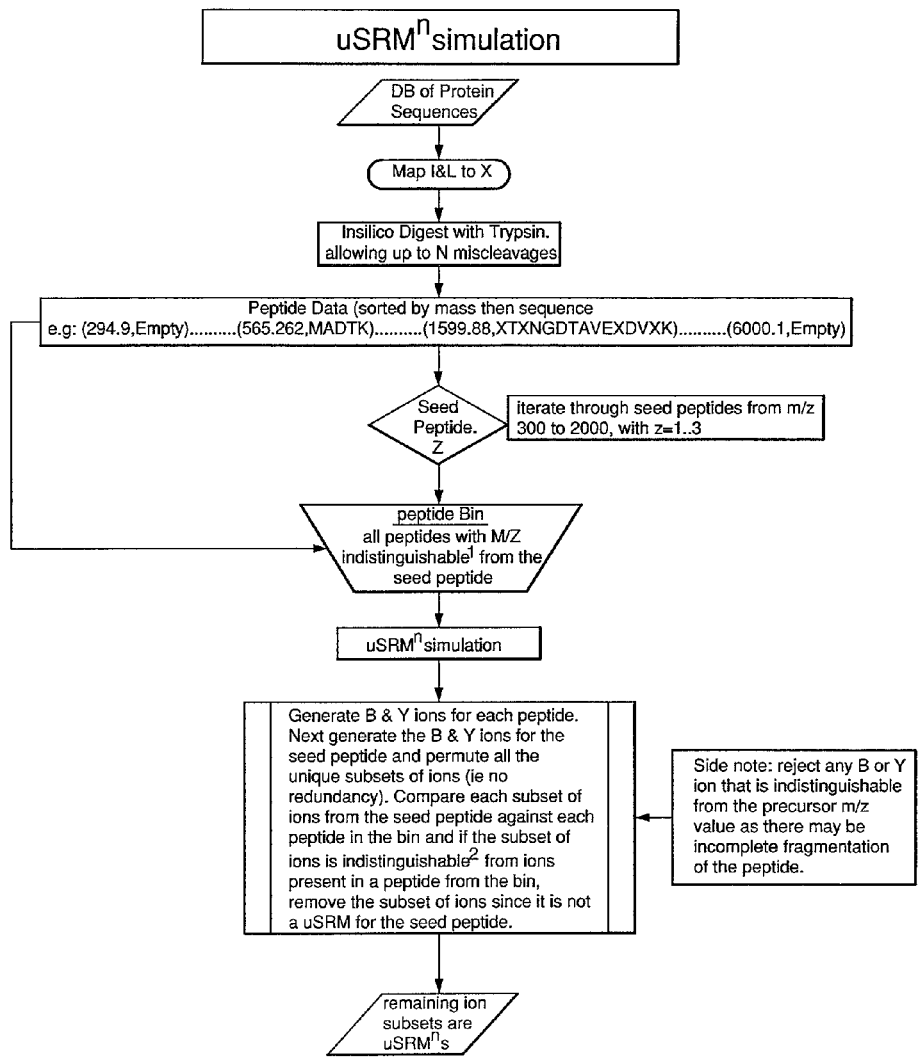
FIG. 3 shows in silico digestion with the proteins in the database with trypsin allowing for 2 missed cleavage sites.

Determining and Assigning Value (or Unique Mass Descriptor; Herein "UMD") to Each Polypeptide of a Proteome 1. Utilize or create a database containing the desired polypeptide sequences. An example would be all the protein sequences in UNIPROT or a subset thereof.
2. Map all the Ile and Leu to X since their masses are indistinguishable.
3. If applicable transform the polypeptides: digest in silico with an enzyme allowing for miscleavage and potentially endopeptidic and endogenous peptide activity, generate the base as well as any possible modified AA sequences (combinatorially if necessary). FIG. 3 illustrates this with example values of N tryptic missed cleavage sites.

4. Group the above generated peptides into a set concurrently checking if the sequences are unique in the set, S.

5. Select a seed peptide $P_i$.

6. G is the subset of S, such that g∈G, g≠$P_i$, that satisfy |mz($P_i$)−mz(g)|≦δ, where δ is the smallest difference detectable by the mass spectrometer being used for the analysis and mz(x) is the m/z value of x. For example, select all the peptides that have an m/z value indistinguishable from $P_i$.

7. For each peptide in G, generate the ions created by CID (for our example b and y ions).

8. A) USRM1: Compare the CID ions of $P_i$ against the CID ions for each of the peptides in G and if the ions are indistinguishable then increment the count for that ion in $P_i$ by one.

B) USRM2: generate all non-redundant pairs (2-combinations) of CID ions of P. Each pair is then compared against each peptide in G. If the pair of ions from $P_i$ are indistinguishable from ions present in the peptide in G, then the count for that pair of ions in $P_i$ is incremented by one.

C) USRMn: generate all n-combinations* of the CID ions from $P_i$. Each n-combination is then compared against each peptide in G. If the ions in the n-combination are indistinguishable from ions present in the peptide, the count for that n-combination of ions in $P_i$ is incremented by one.

*Definition: If S is a set of ions, then a subset of S containing n elements is called an n-combination.

9. (A) If Pi has an ion (1-combination) with a count of zero, then the ion when combined with the peptide m/z value (m/z ($P_i$)) in Step (6)) is a UMD.

(B) If Pi has a pair of ions (2-combination) with a count of zero, then the pair of ions when combined with the peptide m/z value (m/z($P_i$) in Step (6)) is a UMD.

(C) If Pi has an n-combination of ions with a count of zero, then the n-combination when combined with the peptide m/z value (m/z($P_i$) in Step (6)) is a UMD.

An example of this methodology is shown in FIG. 3.

Example 2

Detection of Recombinant Protein Expression

Figure 4:
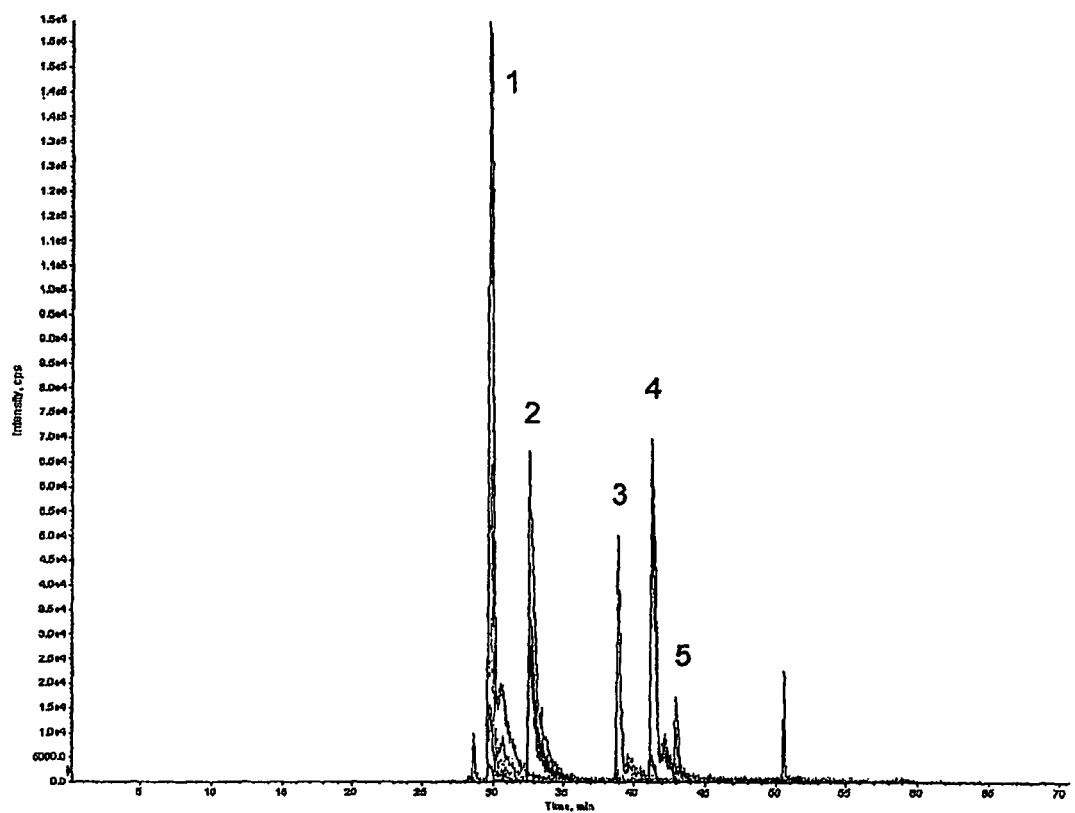
FIG. 4: USRM2 assays detect five tryptic peptides from TBR1 using multiple UMD for each peptide. The detected peptides labelled above are shown in Table 1 and include (1) TLSQLSQQEGIK, (2) TIVLQESIGK, (3) YTVTVEGMIK, (4) EAEIYQTVMLR, (5) YMAPEVLDDSINMK.
Figure 5:
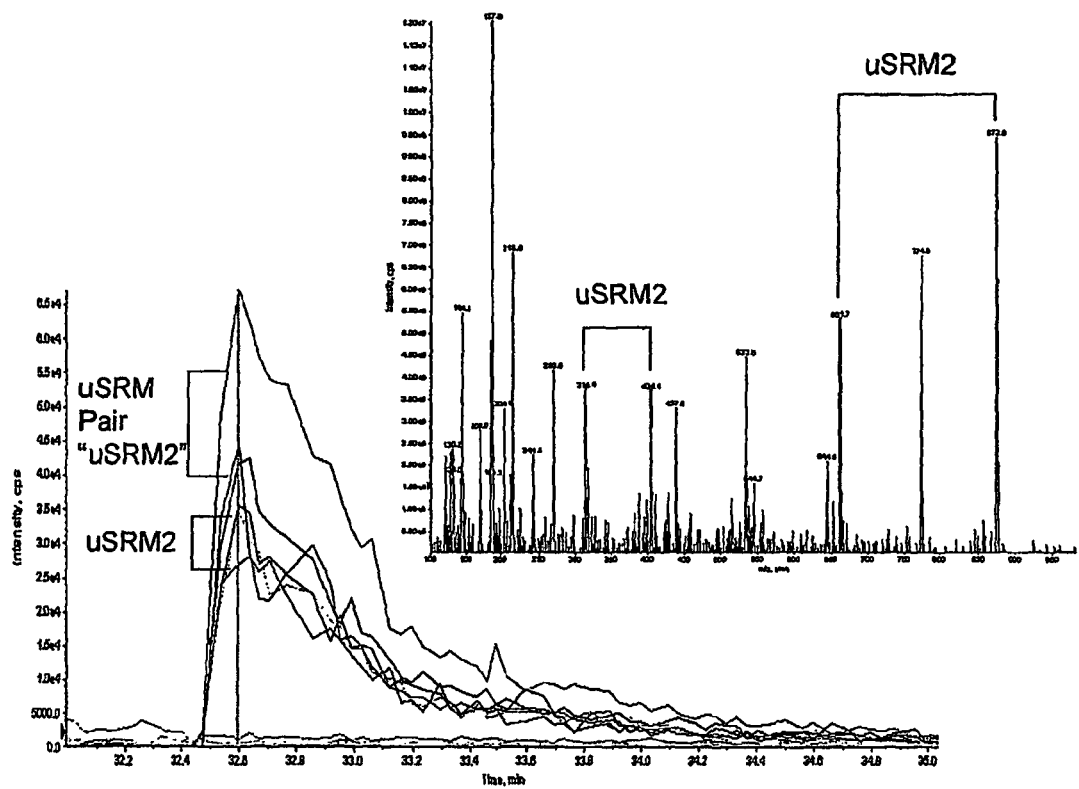
FIG. 5: Detection of TIVLQESIGK from TBR1 using two USRM2 assays. Lower left panel illustrates peaks for two USRM2 assays for the targeted detection of TIVLQESIGK. Upper right panel is the product ion scan triggered to confirm the detection of TIVLQESIGK. Two USRM2 assays for TIVLQESIGK correspond to Table 1.

The method of the present invention (USRM) can specifically detect expression of recombinant target proteins from complex protein mixtures. In this example, a construct of human transforming growth factor beta receptor type-1 (TBR1) was expressed in *E. coli* and subsequently detected using the method. UMD for selected tryptic peptides of TBR1 in a background of the *E. coli* proteome was calculated (Table 1). *E. coli* cells were lysed, digested with trypsin, prepared for MS analysis and injected into the MS. USRM2 assays utilising Q1, and Q3a, Q3b values from Table 1 were used to configure the MS and detect five peptides from TBR1 in a single MS run (FIGS. 4 and 5). Tandem MS and database matching was used to confirm the identity of the peptide TIVLQESIGK (FIG. 2).

Methods

Calculation of Unique Mass descriptors (UMD):

The *E. coli* proteome was downloaded from SWISS-PROT release 51.6. and the sequence for the TBR1 construct added to the database. A set of variables was used for the calculation that included: the order of the USRMs (one Q1 and two Q3 values), use of trypsin for proteolysis, the number of possible missed cleavage sites set at 2, possible modifications of certain amino acids (oxidation of methionine and reduction of cysteine), the number of allowed charge states (+1, +2, +3), and the number of heavy isotopes to consider (+1, . . . +5 amu). Using this description all the possible peptides were generated, X was substituted for isoleucine and leucine, and the peptides then mapped into a set. If the peptide being loaded was already present in the set it was marked as redundant and excluded as a candidate having a UMD. From this set the peptides that contain no inappropriate cleavage residues and are non-redundant in the proteome and fall within a 300-2000 m/z domain were candidates for potential UMD addresses. For each candidate peptide, all charged peptides within a given tolerance (e.g. +/−1 m/z) were pooled. From the pooled peptides, the candidate peptide's fragment ions were generated (i ions), and all the possible combinations of Q3 m/z were considered. For a USRMr (r=1 or 2) the number of candidate addresses is given by (i choose r)=i!/((r!)(i−r)!). These candidates were then challenged with all the combinations of fragment ions for each of the peptides in the pool. Non unique peptides were removed by determining if all Q3 values in a combination have a counterpart challenge combination where the ions are within a tolerance (e.g. +/−1 m/z) of a candidate combination. All remaining peptide fragments were considered unique and comprise a unique mass descriptor (UMD) consisting of a Q1 value and two Q3 values.

TABLE 1

USRM2 assays used to detect 5 peptides from TBR1 expressed in *E. coli*.

| Peptide[a] | Peptide Sequence | USRM2 Q1 | Q3a, Q3b |
|---|---|---|---|
| 1 | TLSQLSQQEGIK | 666.4 | 317.2, 789.4 |
| | | 666.4 | 317.2, 1030.6 |
| | | 666.4 | 317.2, 1117.6 |
| | | 666.4 | 543.3, 702.4 |
| | | 666.4 | 574.3, 789.4 |
| | | 666.4 | 574.3, 1030.6 |
| 2 | TIVLQESIGK | 544.3 | 314.2, 317.2 |
| | | 544.3 | 314.2, 404.3 |
| | | 544.3 | 404.3, 661.3 |
| | | 544.3 | 404.3, 774.4 |
| | | 544.3 | 661.3, 873.5 |
| 3 | YTVTVEGMIK | 570.8 | 448.3, 977.5 |
| | | 570.8 | 577.3, 977.5 |
| | | 570.8 | 777.4, 977.5 |
| 4 | EAEIYQTVMLR | 676.8 | 419.2, 910.5 |
| | | 676.8 | 419.2, 1023.6 |
| | | 676.8 | 419.2, 1152.6 |
| | | 676.8 | 518.3, 910.5 |
| | | 676.8 | 518.3, 1023.6 |

TABLE 1-continued

USRM2 assays used to detect 5 peptides from TBR1 expressed in *E.coli*.

| Peptide[a] | Peptide Sequence | USRM2 Q1 | Q3a, Q3b |
|---|---|---|---|
| | | 676.8 | 619.4, 910.5 |
| | | 676.8 | 619.4, 1152.6 |
| | | 676.8 | 747.4, 1023.6 |
| | | 676.8 | 747.4, 1152.6 |
| | | 676.8 | 747.4, 1223.6 |
| | | 676.8 | 910.5, 1152.6 |
| | | 676.8 | 910.5, 1223.6 |
| 5 | YMAPEVLDDSINMK | 813.4 | 366.1, 392.2 |
| | | 813.4 | 366.1, 822.4 |
| | | 813.4 | 392.2, 935.5 |
| | | 813.4 | 392.2, 1163.6 |
| | | 813.4 | 392.2, 1331.6 |
| | | 813.4 | 592.3, 804.4 |
| | | 813.4 | 592.3, 822.4 |
| | | 813.4 | 707.3, 1260.6 |
| | | 813.4 | 804.4, 1331.6 |

[a]Peptide numbers correspond to chromatographic peaks in FIG. 4.

Bacterial Expression of TBR1

E. coli expressing a His-tagged cytoplasmic domain human TGF-beta receptor 1 construct as shown below was grown in LB media to mid log phase ($A_{600}$=1.2) and collected by centrifugation. The cells were washed with 100 mM Tris/HCl (pH 8.0), then resuspended in 100 mM Tris/HCl (pH 8), supplemented with protease inhibitors. The cells were lysed using a French press operated at 12000 psi.

```
TBR1 construct
MHHHHHHSSGLVPRGSGMKETAAAKFERQHMDSPDLGTDDDDKAMGYLWI

CHNRTVIHHRVPNEEDPSLDRPFISEGTTLKDLIYDMTTSGSGSGLPLLV

QRTIARTIVLQESIGKGRFGEVWRGKWRGEEVAVKIFSSREERSWFREAE

IYQTVMLRHENILGFIAADNKDNGTWTQLWLVSDYHEHGSLFDYLNRYTV

TVEGMIKLALSTASGLAHLHMEIVGTQGKPAIAHRDLKSKNILVKKNGTC

CIADLGLAVRHDSATDTIDIAPNHRVGTKRYMAPEVLDDSINMKHFESFK

RADIYAMGLVFWEIARRCSIGGIHEDYQLPYYDLVPSDPSVEEMRKVVCE

QKLRPNIPNRWQSCEALRVMAKIMRECWYANGAARLTALRIKKTLSQLSQ

QEGIKM
```

Sample Preparation of TBR1 for MS Analysis

100 µL of cell lysate was reduced for 1 hour at 65° C. using DTT by adjusting the concentration of DTT to 5 mM. Following reduction, proteins were alkylated for 1 hour by the addition of IAA to a concentration of 12.5 mM. Reduced and alkylated protein samples (approximately 100 µL) were diluted with 400 µL of 20 mM ammonium bicarbonate containing 20 µg of trypsin and digested for 18 hours at 37° C.

Liquid Chromatography and Mass Spectrometry Analysis:

Digested protein samples (10 µL) were analysed using a 4000 QTRAP hybrid triple quadrupole/linear ion trap mass spectrometer (Applied Biosystems, Foster City, Calif., USA) operating in positive ion mode. Peptides were separated by nanoflow liquid chromatography using an Eksigent 2D LC system (Eksigent Technologies, Dublin, Calif., USA). Digested samples were analysed by injecting 10 µL of the digest onto a precolumn (Captrap 0.5×2 mm, Michrom BioResources Inc, Auburn, Calif., USA) for preconcentration with 95:5 mobile phase A:mobile phase B (mobile phase A: 2% v/v acetonitrile containing 0.1% v/v formic acid, mobile phase B: 80% v/v acetonitrile containing 0.1% v/v formic acid) at 10 µl/min. Peptides were then separated using a ProteCol C18 column (300 Å, 3 µm, 150 µm×10 cm, SGE Analytical Sciences, Ringwood, Victoria, Australia). Peptides were eluted from the column using a linear gradient from 95:5 mobile phase A:mobile phase B to 45:55 mobile phase A:mobile phase B over 60 minutes at a flowrate of 600 nL/min. The LC eluent was subject to positive ion nanoflow analysis using a NanoSpray II source equipped with a MicroIonSpray II spray head. Column eluent was directed into the MicroIonSpray II spray head via coupling to a distal coated PicoTip fused silica spray tip (360 µm OD, 75 µm ID, 15 µm diameter emitter orifice, New Objective, Woburn, Mass., USA). uSRM experiments conducted for each peptide used unit resolution settings for Q1 and Q3. Samples were analysed using an ion spray voltage, heater interface temperature, curtain gas flow, and nebulizing gas flow of 2.1 kV, 150° C., 18, and 12, respectively. Collision energy (CE) was determined using the following equation CE=slope×(m/z)+intercept, where, slope=0.050 and intercept=5.5 for +2 precursor ions.

USRM2 Scanning:

USRM2 experiments utilised the combination of a precursor ion (Q1), and a pair of product ions (Q3a, Q3b) appropriate for each UMD. Wherever possible, these experiments utilised a primary Q3 value corresponding to the highest intensity product ion that constituted a USRM2 pair and a secondary Q3 value corresponding to the second most intense product ion that constituted the USRM2 pair for each peptide candidate. Additional USRM2s utilising UMD other than the first and second most intense product ion pairs were also assessed wherever possible. USRM2 assays were validated by triggering a product ion scan (MS/MS) when individual SRM signals exceeded 300 cps.

Example 3

Detection of a Polypeptide in Human Blood Plasma

Figure 6:
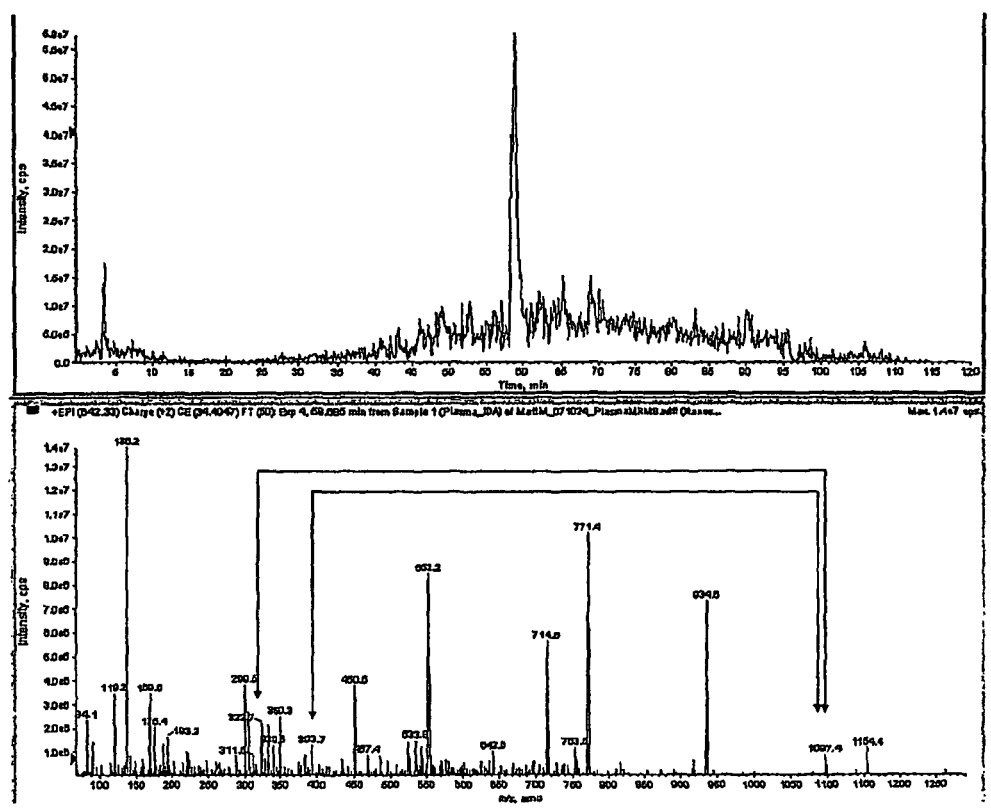
FIG. 6: Detection of the peptide EGYYGYTGAFR from serotransferrin by LC/MS/MS. Top panel shows the extracted ion chromatogram for ions with m/z 643.3. The peak at approximately 59 minutes is for the peptide EGYYGYT-GAFR from serotransferrin as confirmed by UMD. Lower panel contains the MS/MS scan for EGYYGYTGAFR. Fragment ions that constitute the two different UMDs for this peptide are illustrated by double headed arrows.
Figure 7:
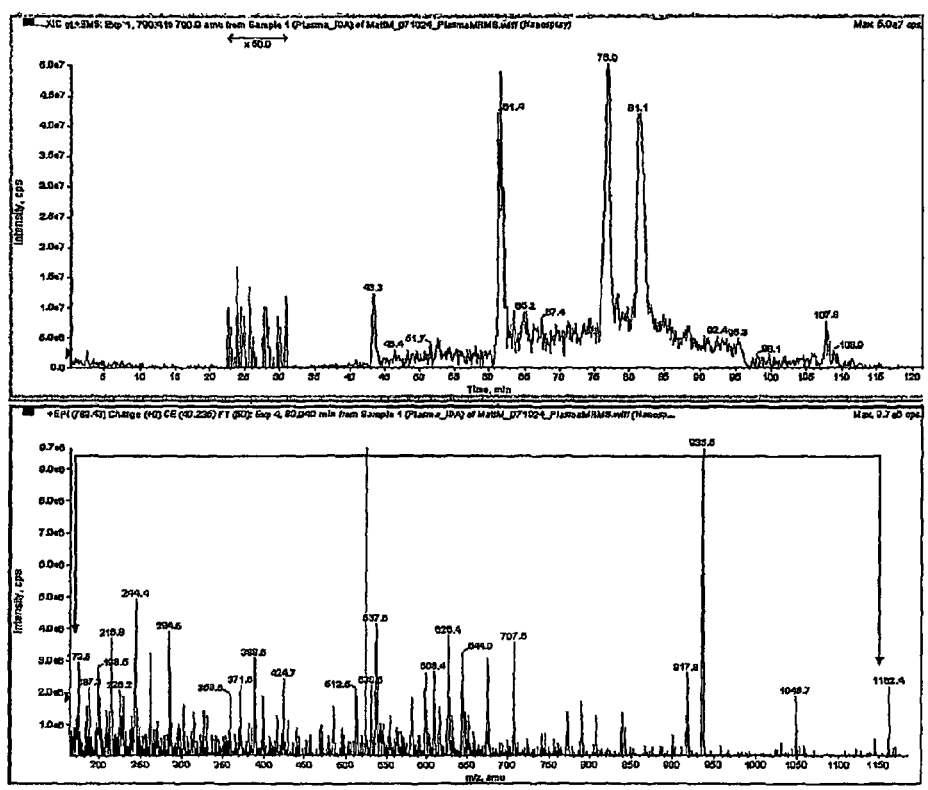
FIG. 7: Detection of the peptide TAGWNIPMGLLYNK from serotransferin by LC/MS/MS. Top panel is the extracted ion chromatogram for ions with m/z 789.4. Approximately five peptides with m/z of 789.4 were detected in plasma with a signal-to-noise ratio greater then 50. The peak at approximately 81 minutes corresponds to the peptide TAGWNIPMGLLYNK from serotransferrin as confirmed by UMD shown in the lower panel. Lower panel contains the MS/MS scan for TAGWNIPMGLLYNK. Fragment ions that constitute the UMD are illustrated by double headed arrows.
Figure 8:
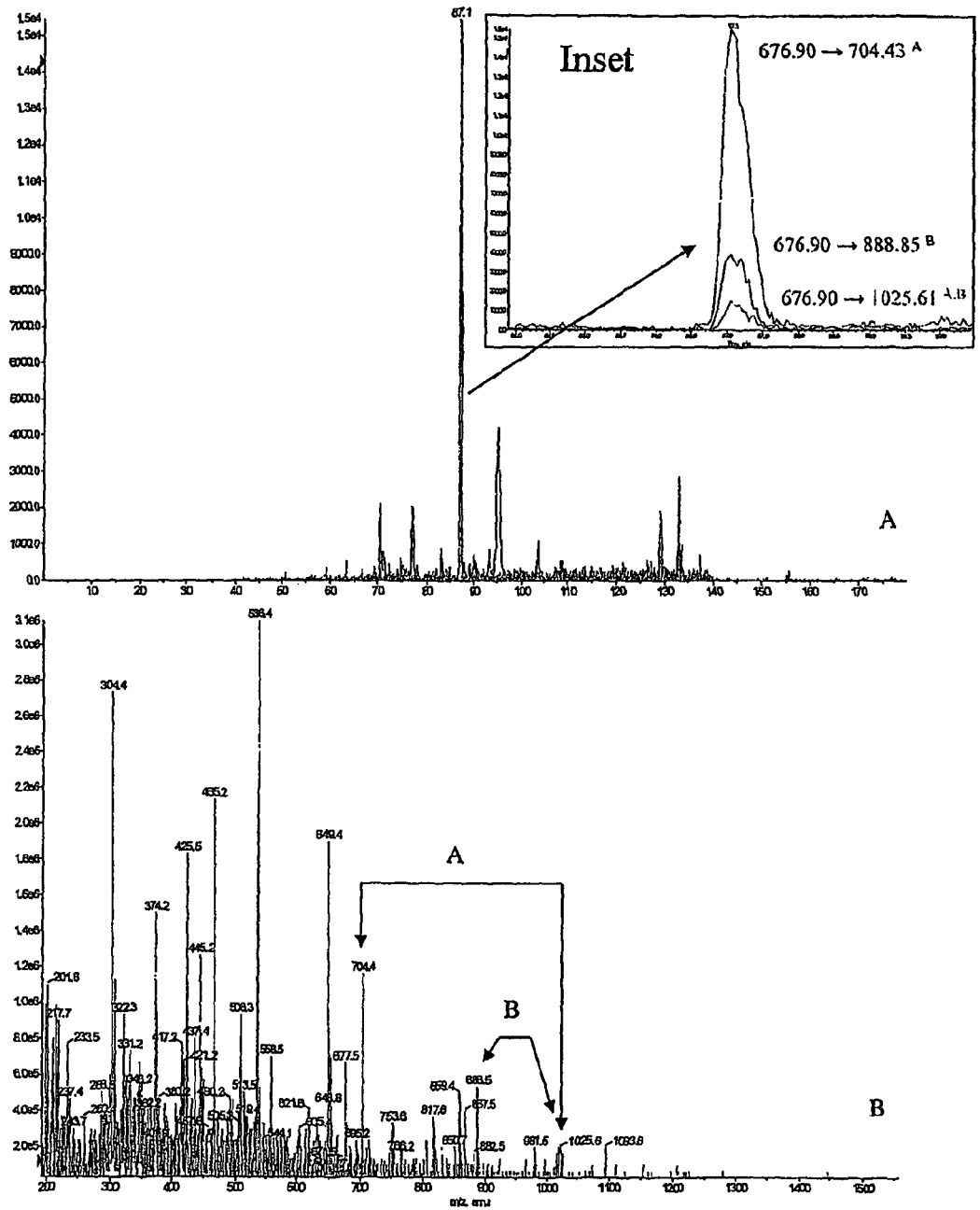
FIG. 8: Selective detection of the peptide DLVHAIPLYAIK in whole cell lysate from the *E. coli* protein aconitate hydratase 2 using unique mass descriptors (UMD). A) Overlaid XICs illustrating the targeted detection of DLVHAIPLYAIK using unique selected reaction monitoring 2 (USRM2). Inset shows an expanded region of the overlaid XICs illustrating the coelution of each USRM2 assay (denoted $^{A,B}$), B) MS/MS spectrum confirming the detection of the peptide DLVHAIPLYAIK in *E. coli* whole cell lysate. Fragment ions constituting USRM2 assays ($^{A,B}$) are indicated.
Figure 9:
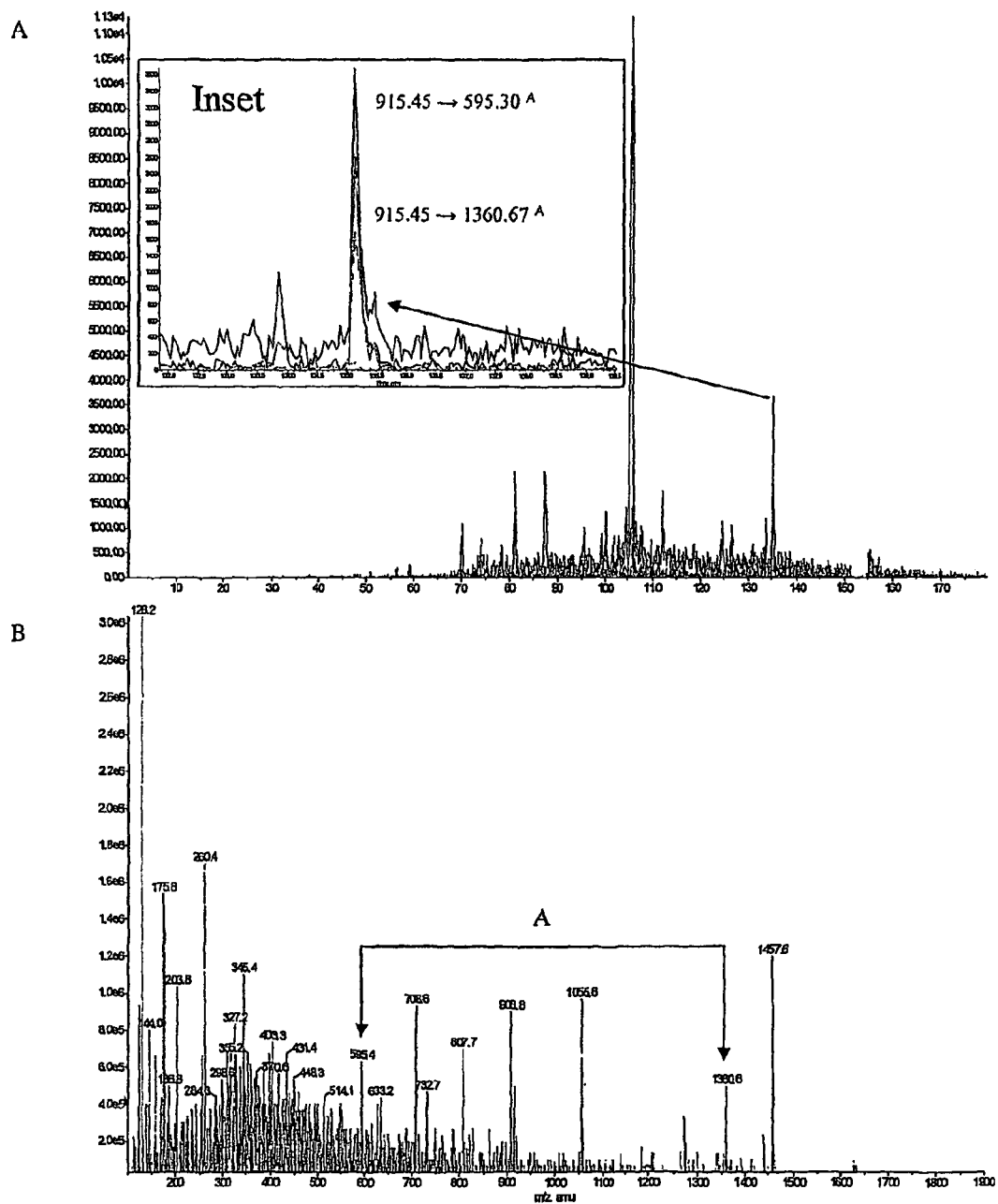
FIG. 9: Selective detection of the peptide AMGIPSSMFTVIFAMAR in whole cell lysate from the *E. coli* protein citrate synthase using unique mass descriptors (UMD). A) Overlaid XICs illustrating the targeted detection of AMGIPSSMFTVIFAMAR using unique selected reaction monitoring 2 (USRM2). Inset shows an expanded region of the overlaid XICs illustrating the coelution of a USRM2 assay (denoted $^{A}$). B) MS/MS spectrum confirming the detection of the peptide AMGIPSSMFTVIFAMAR in *E. coli* whole cell lysate. Fragment ions constituting the USRM2 assay ($^{A}$) are indicated.
Figure 10:
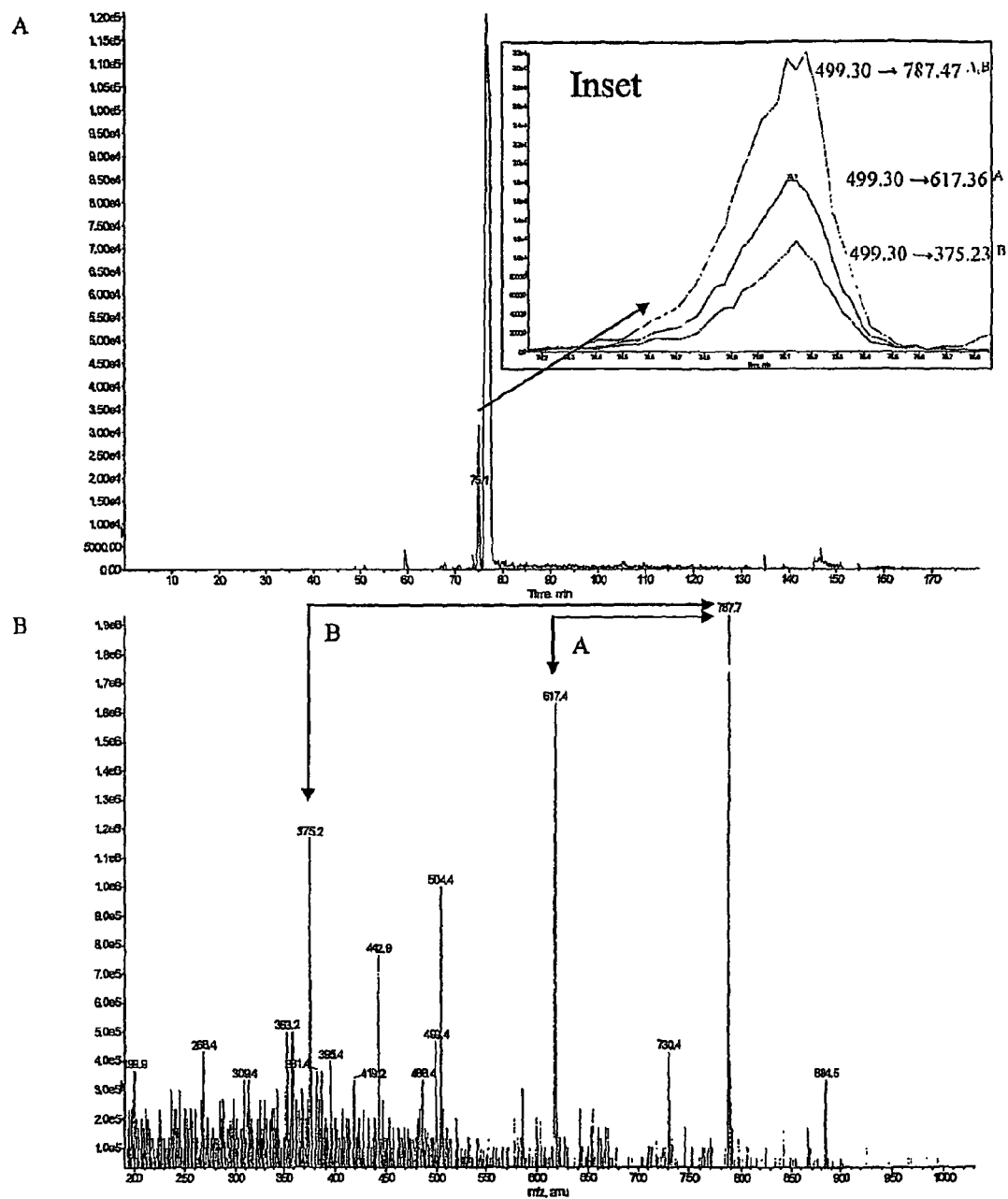
FIG. 10: Selective detection of the LPGILELSR peptide in whole cell lysate from the *E. coli* protein Succinate dehydrogenase flavoprotein subunit using unique mass descriptors (UMD). A) Overlaid XICs illustrating the targeted detection of LPGILELSR using unique selected reaction monitoring 2 (USRM2). Inset shows an expanded region of the overlaid XICs illustrating the coelution of each USRM2 assay (denoted $^{A,B}$). B) MS/MS spectrum confirming the detection of the peptide LPGILELSR in *E. coli* whole cell lysate. Fragment ions constituting each USRM2 assay ($^{A,B}$) are indicated.
Figure 11:
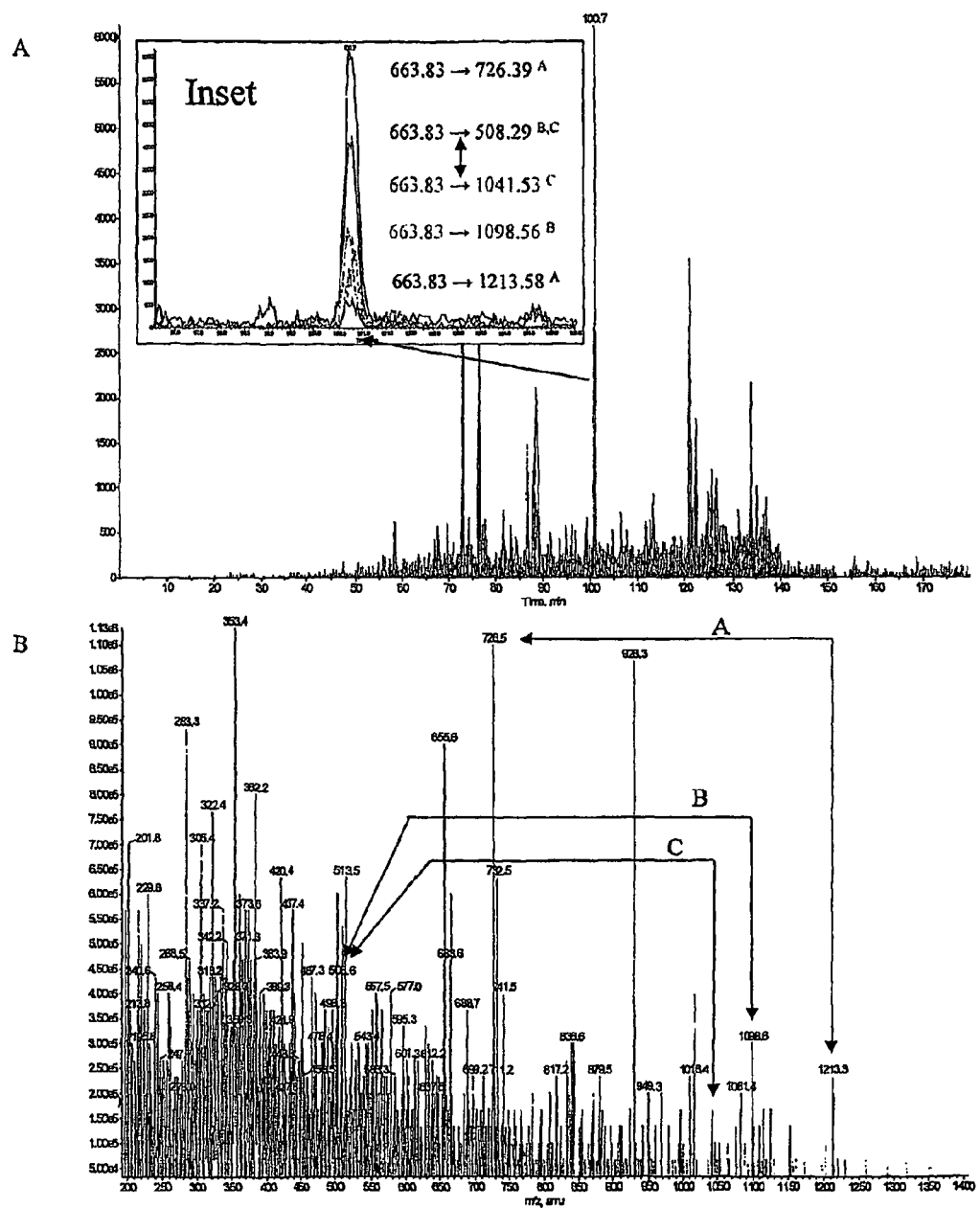
FIG. 11: Selective detection of the peptide LDGLSDAFSVFR in whole cell lysate from the *E. coli* protein Succinate dehydrogenase iron-sulfur subunit using unique mass descriptors (UMD). A) Overlaid XICs illustrating the targeted detection of LDGLSDAFSVFR using unique selected reaction monitoring 2 (USRM2). Inset shows an expanded region of the overlaid XICs illustrating the coelution of each USRM2 assay (denoted $^{A,B,C}$). B) MS/MS spectrum confirming the detection of the peptide LDGLSDAFSVFR in *E. coli* whole cell lysate. Fragment ions constituting each USRM2 pair ($^{A,B,C}$) are indicated.
Figure 12:
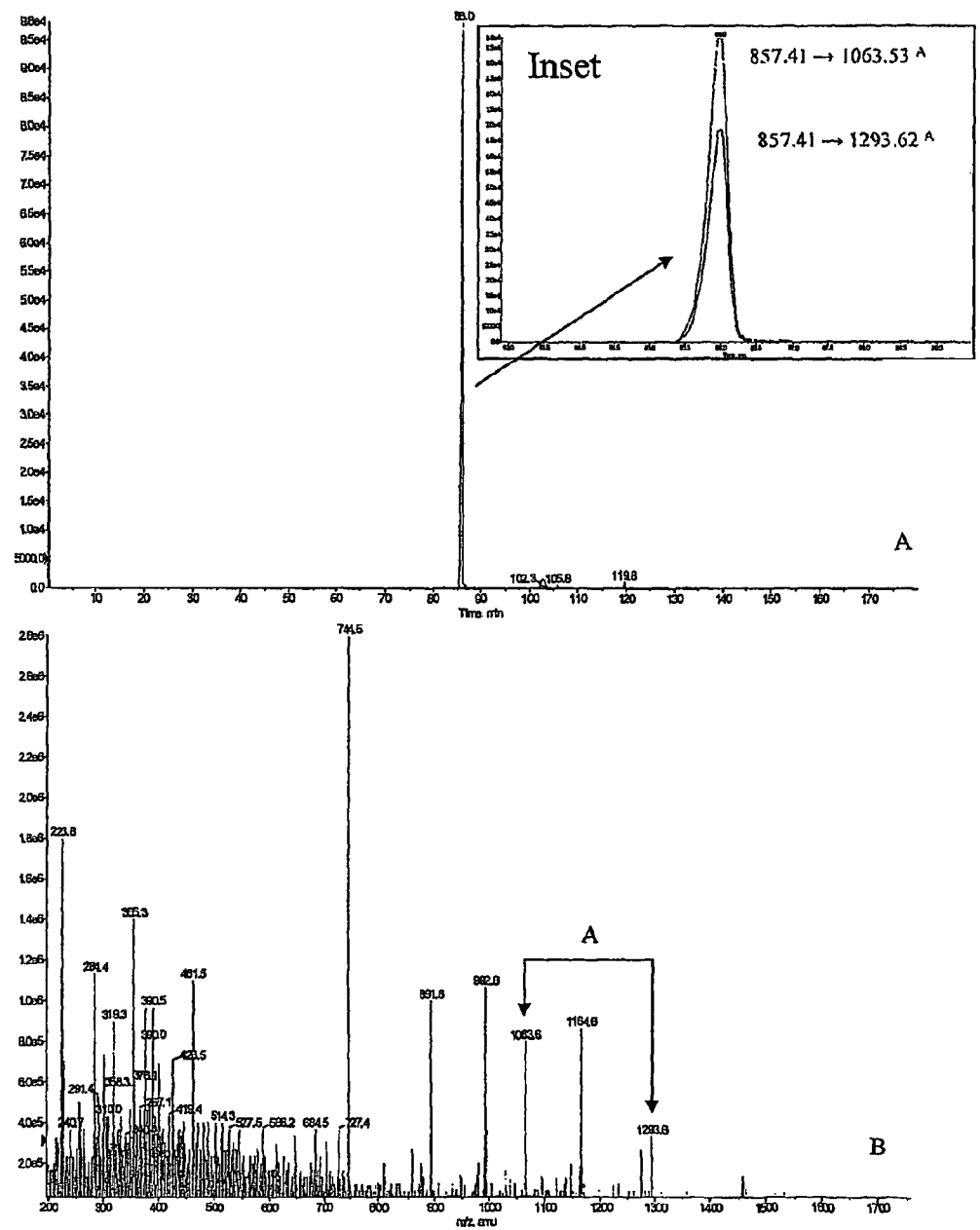
FIG. 12: Selection detection of the peptide GISYETATFPWAASGR in whole cell lysate from the *E. coli* protein Dihydrolipoyl dehydrogenase using unique mass descriptors (UMD). A) Overlaid XICs illustrating the targeted detection of GISYETATFPWAASGR using unique selected reaction monitoring 2 (USRM2). Inset shows an expanded region of the overlaid XICs illustrating the coelution of a USRM2 assay (denoted $^{A}$). B) MS/MS spectrum confirming the detection of the peptide GISYETATFPWAASGR in *E. coli* whole cell lysate. Fragment ions constituting the USRM2 assay ($^{A}$) are indicated.
Figure 13:
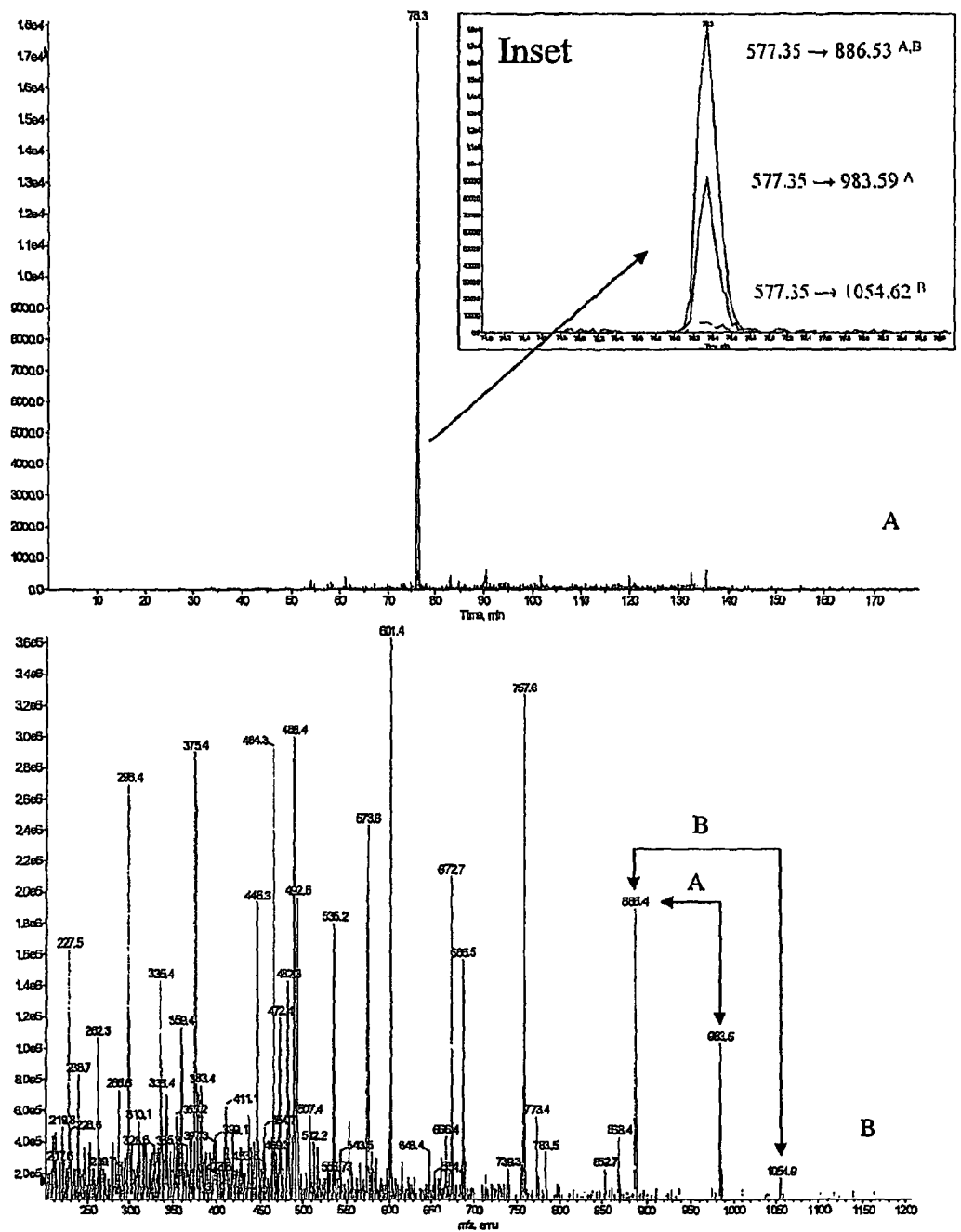
FIG. 13: Selective detection of the peptide VAPEALTLLAR in whole cell lysate from the *E. coli* protein Fumarate hydratase class 1, aerobic using unique mass descriptors (UMD). A) Overlaid XICs illustrating the targeted detection of VAPEALTLLAR using unique selected reaction monitoring 2 (USRM2). Inset shows an expanded region of the overlaid XICs illustrating the coelution of each USRM2 assays (denoted $^{A,B}$). B) MS/MS spectrum confirming the detection of the peptide VAPEALTLLAR in *E. coli* whole cell lysate. Fragment ions constituting each USRM2 assay ($^{A,B}$) are indicated.
Figure 14:
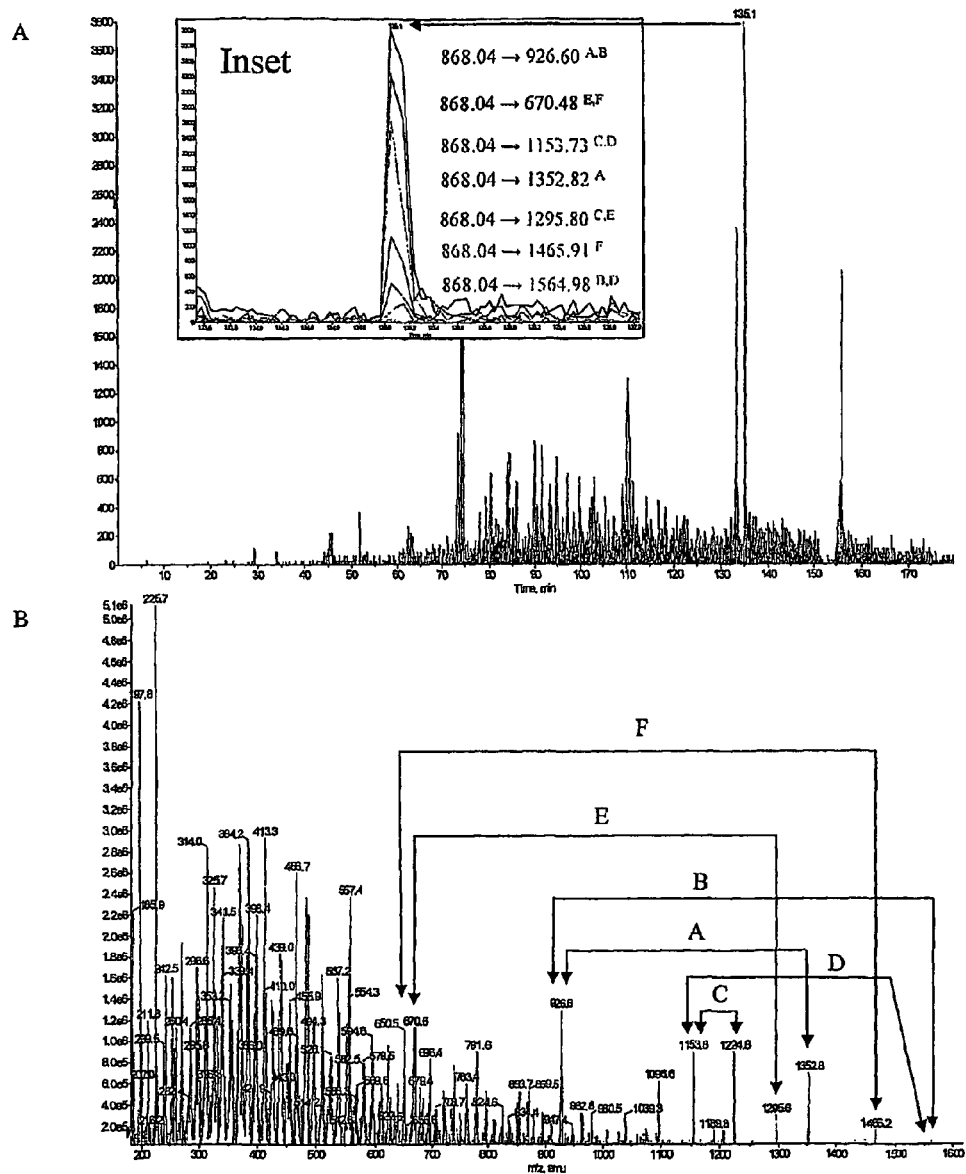
FIG. 14: Selective detection of the peptide VAVLGAAGGIGQALALLLK in whole cell lysate from the *E. coli* protein Malate dehydrogenase using unique mass descriptors (UMD). A) Overlaid XICs illustrating the targeted detection of VAVLGAAGGIGQALALLLK using unique selected reaction monitoring 2 (USRM2). Inset shows an expanded region of the overlaid XICs illustrating the coelution of each USRM2 assay (denoted $^{A,B,C,D,E,F}$). B) MS/MS spectrum confirming the detection of the peptide VAVLGAAGGIGQALALLLK in *E. coli* whole cell lysate. Fragment ions constituting each USRM2 assay ($^{A,B,C,D,E,F}$) are indicated.
Figure 15:
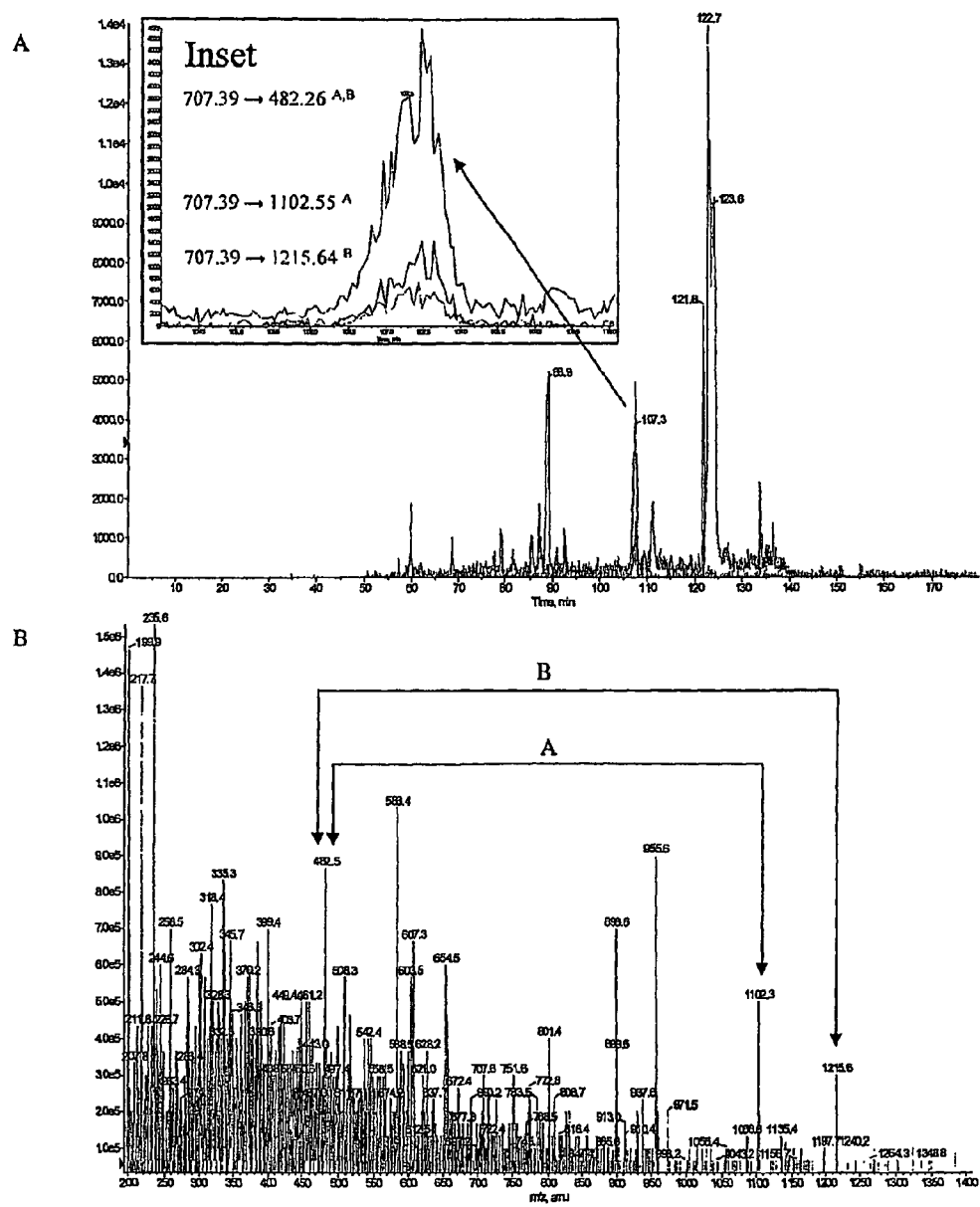
FIG. 15: Selective detection of the peptide VVLFGPFATFSTK in whole cell lysate from the *E. coli* protein malate: quinone oxidoreducatase using unique mass descriptors (UMD). A) Overlaid XICs illustrating the targeted detection of VVLFGPFATFSTK using unique selected reaction monitoring 2 (USRM2). Inset shows an expanded region of the overlaid XICs illustrating the coelution of each USRM2 assay (denoted $^{A,B}$). B) MS/MS spectrum confirming the detection of the peptide VVLFGPFATFSTK in *E. coli* whole cell lysate. Fragment ions constituting each USRM2 assay ($^{A,B}$) are indicated.
Figure 16:
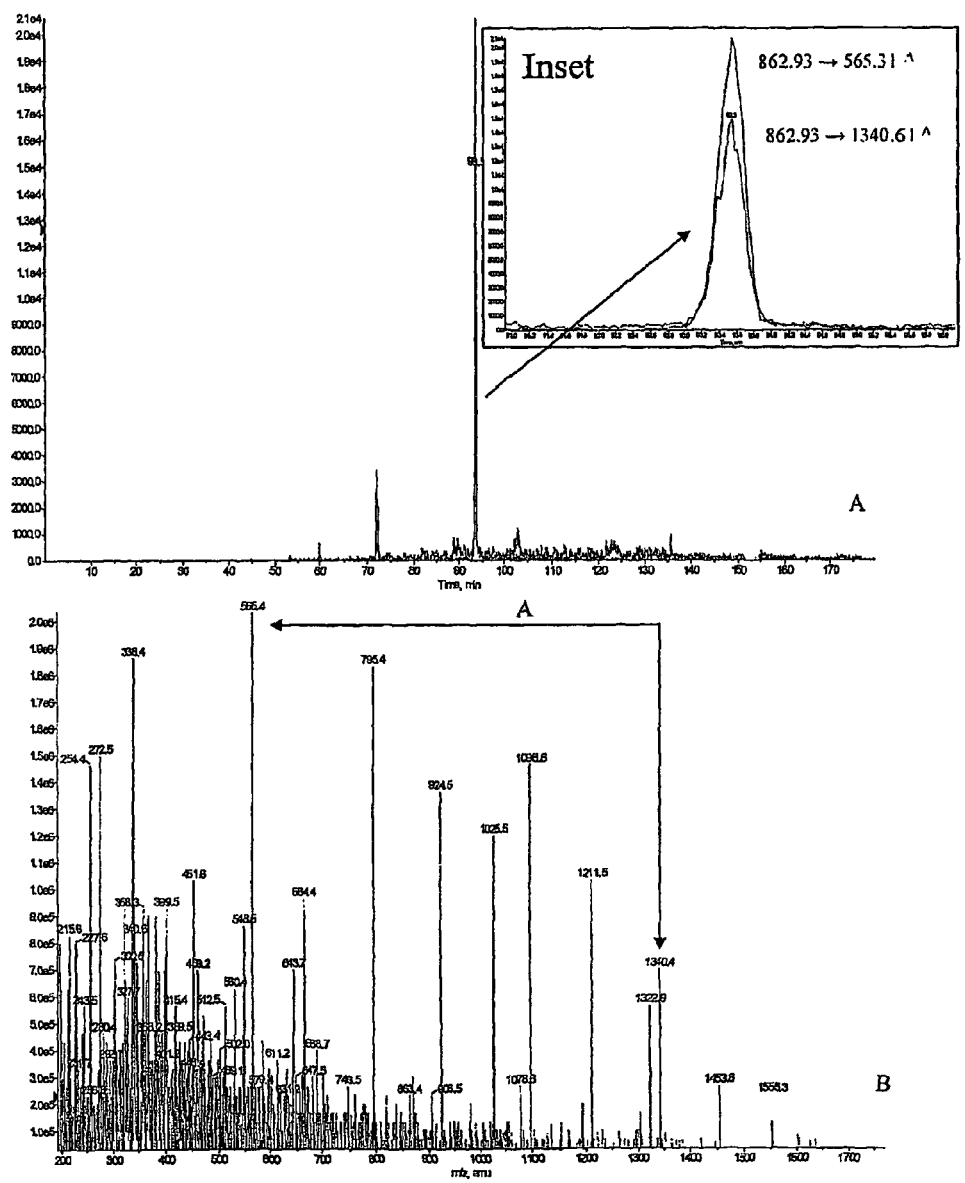
FIG. 16: Selective detection of the peptide VATLEDATEMVNLYR in whole cell lysate from the *E. coli* protein 2-oxoglutarate dehydrogenase E1 component using unique mass descriptors (UMD). A) Overlaid XICs illustrating the targeted detection of VATLEDATEMVNLYR using unique selected reaction monitoring 2 (USRM2). Inset shows an expanded region of the overlaid XICs illustrating the coelution of a USRM2 assay (denoted $^{A}$). B) MS/MS spectrum confirming the detection of the peptide VATLEDATEMVNLYR in *E. coli* whole cell lysate. Fragment ions constituting the USRM2 assay ($^{A}$) is indicated.
Figure 17:
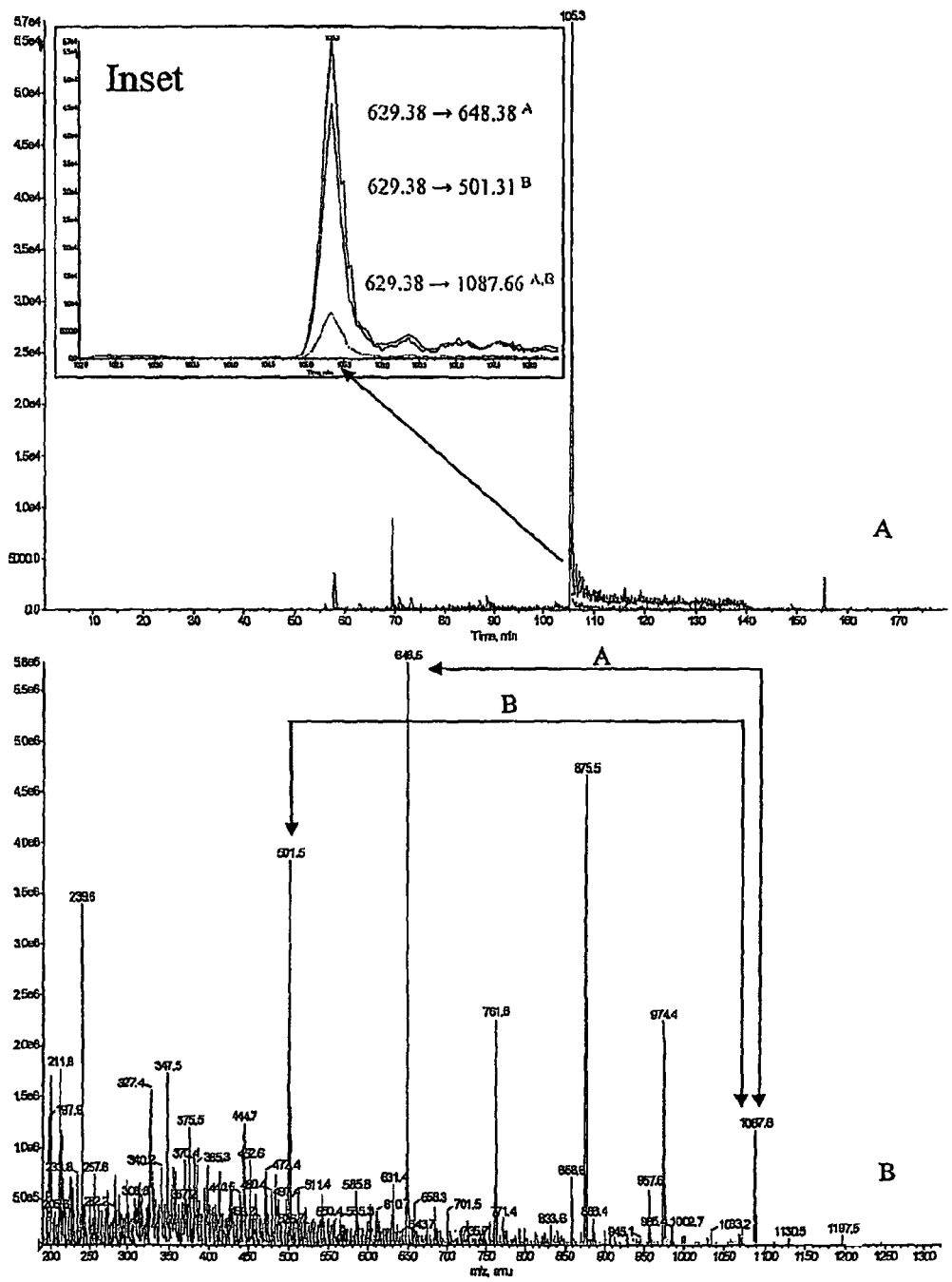
FIG. 17: Selective detection of the peptide AVLVNIFGGIVR in whole cell lysate from the *E. coli* protein Succinyl-CoA synthesase beta chain using unique mass descriptors (UMD). A) Overlaid XICs illustrating the targeted detection of AVLVNIFGGIVR using unique selected reaction monitoring 2 (USRM2). Inset shows an expanded region of the overlaid XICs illustrating the coelution of each USRM2 assay (denoted $^{A,B}$). B) MS/MS spectrum confirming the detection of the peptide AVLVNIFGGIVR in *E. coli* whole cell lysate. Fragment ions constituting the USRM2 assays ($^{A,B}$) are indicated.
Figure 18:
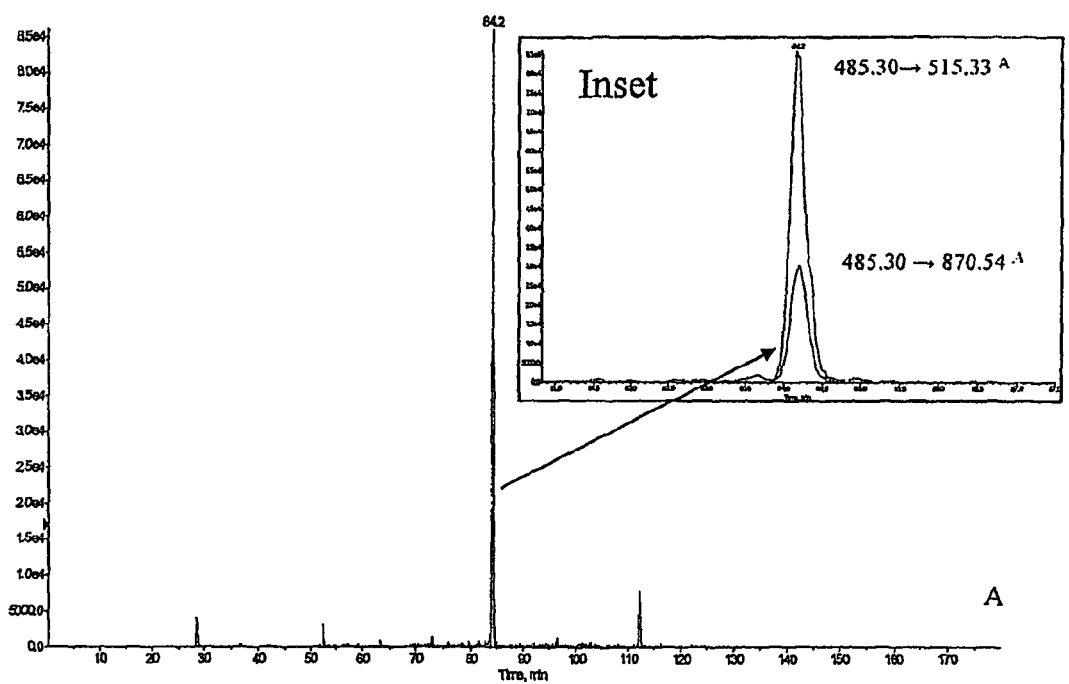
FIG. 18: Selective detection of the peptide VLLENLLR in whole cell lysate from the *E. coli* protein Aconitate hydratase 1 using unique mass descriptors (UMD). A) Overlaid XICs illustrating the targeted detection of VLLENLLR using unique selected reaction monitoring 2 (USRM2). Inset shows an expanded region of the overlaid XICs illustrating the coelution of a USRM2 assay (denoted $^{A}$). The detection of VLLENLLR could not be independently confirmed since an MS/MS scan was not triggered at 83.7 minutes for the ion at 485.3 amu.
Figure 19:
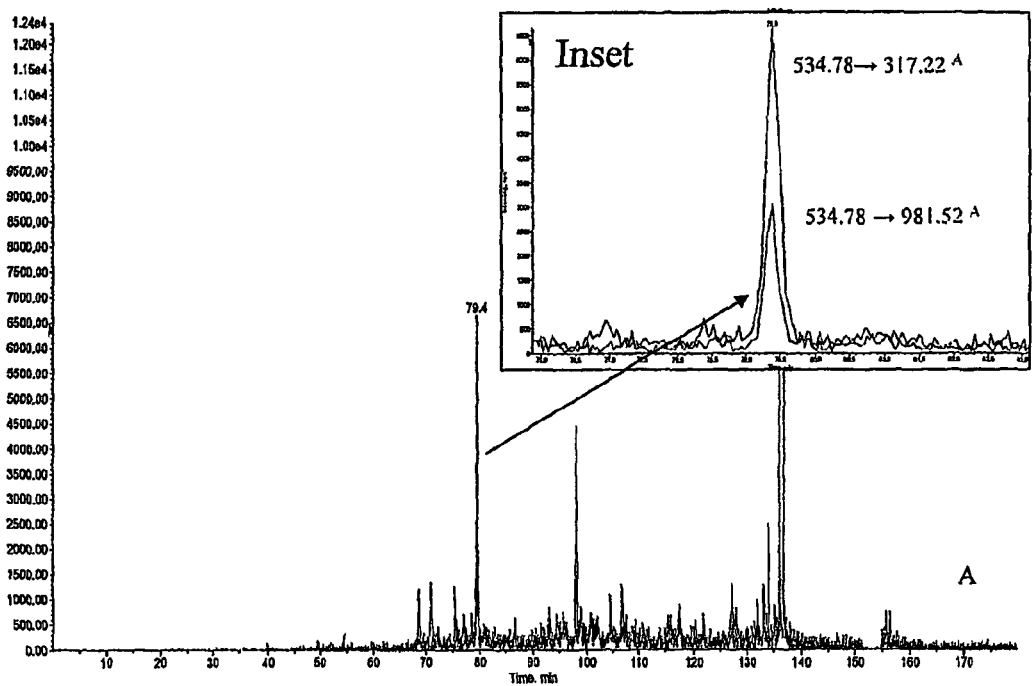
FIG. 19: Selective detection of the peptide SGTLTYEAVK in whole cell lysate from the E. coli protein Succinyl-CoA ligase [ADP-forming] subunit alpha using unique mass descriptors (UMD). A) Overlaid XICs illustrating the targeted detection of SGTLTYEAVK using unique selected reaction monitoring 2 (USRM2). Inset shows an expanded region of the overlaid XICs illustrating the coelution of 2 USRM2 pairs represented by double headed arrow (↔). The detection of SGTLTYEAVK could not be independently confirmed since an MS/MS scan was not triggered at 79.4 minutes for the ion at 534.8 amu.
Figure 20:
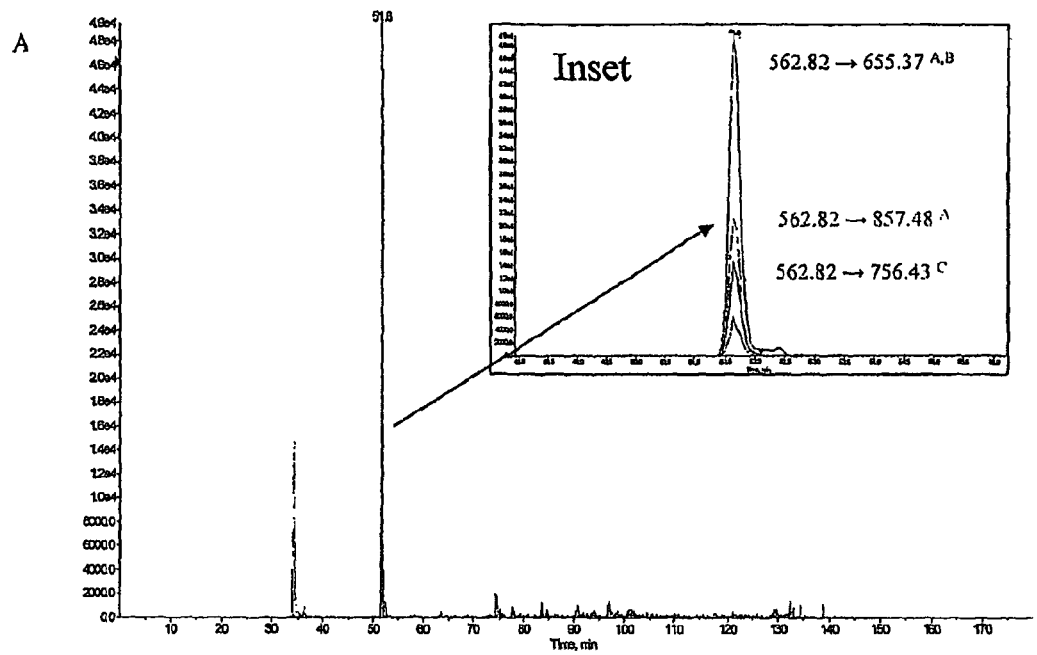
FIG. 20: Selective detection of the peptide GPLTTPVGGIR in whole cell lysate from the E. coli protein isocitrate dehydrogenase [NADP] using unique mass descriptors (UMD). A) Overlaid XICs display the targeted detection of GPLTTPVGGIR using unique selected reaction monitoring 2 (USRM2). Inset shows an expanded region of the overlaid XICs illustrating the coelution each USRM2 assay (denoted A,B,C). B) MS/MS spectrum confirming the detection of the peptide GPLTTPVGGIR in E. coli whole cell lysate. Fragment ions constituting a USRM2 pair (A,B,C) are indicated.
Figure 20:
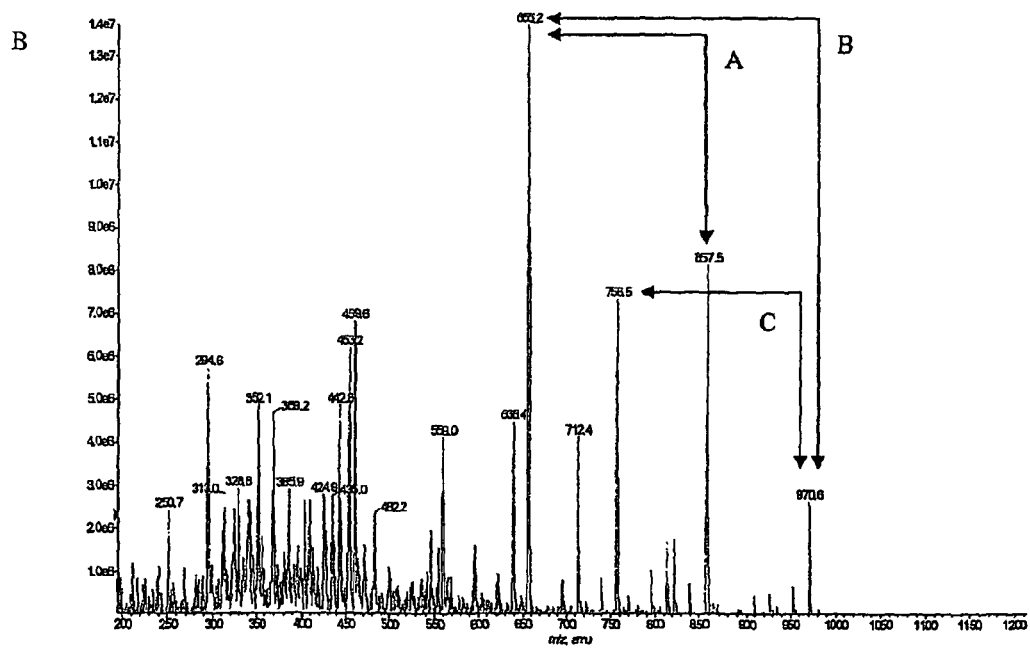

The method of the present invention (USRM) is compatible with detection of protein biomarkers in blood for in vitro diagnostic purposes. The method was demonstrated by specific detection of two peptides from serotransferrin in human plasma. Plasma was immunodepleted to remove albumin and IgG, digested with trypsin, prepared for MS analysis and injected into the MS. USRM2 assays utilising Q1, and Q3a, Q3b values from the UMD calculation were used to configure the MS and detect two peptides from serotransferrin in a single MS run (FIGS. 6 and 7). Tandem MS and database matching was used to confirm the identity of the peptides as shown in Table 2.

Methods
Calculation of Unique Mass Descriptors (UMD):

The human proteome was downloaded from SWISS-PROT release 51.6. A set of variables was used for the calculation that included: the order of the USRMs (one Q1 and two Q3 values), use of trypsin for proteolysis, the number of possible missed cleavage sites set at 2, possible modifications of certain amino acids (oxidation of methionine and reduction of cysteine), the number of allowed charge states (+1, +2, +3), and the number of heavy isotopes to consider (+1, . . . +5 amu). Using this description all the possible peptides were generated, X was substituted for isoleucine and leucine, and the peptides then mapped into a set. If the peptide being loaded was already present in the set it was marked as redundant and excluded as a candidate having a UMD. From this set the peptides that contain no inappropriate cleavage residues and are non-redundant in the proteome and fall within a 300-2000 m/z domain were candidates for potential UMD addresses. For each candidate peptide, all charged peptides within a given tolerance (e.g. +/−1 m/z) were pooled. From the pooled peptides, the candidate peptide's fragment ions were generated (i ions), and all the possible combinations of Q3 m/z were considered. For a USRMr (r=1 or 2) the number of candidate addresses is given by (i choose r)=i!/((r!)(i−r)!). These candidates were then challenged with all the combinations of fragment ions for each of the peptides in the pool. Non unique peptides were removed by determining if all Q3 values in a combination have a counterpart challenge combination where the ions are within a tolerance (e.g. +/−1 m/z) of a candidate combination. All remaining peptide fragments were considered unique and comprise a unique mass descriptor (UMD) consisting of a Q1 value and two Q3 values.

TABLE 2

Selected UMDs for the peptide sequences EGYYGYTGAFR and TAGWNIPMGLLYNK from human serotransferrin.

| Peptide sequence | Q1 | Q3a | Q3b |
| --- | --- | --- | --- |
| EGYYGYTGAFR | 642.3 | 322.2 | 1097.5 |
|  | 642.3 | 393.2 | 1097.5 |
| TAGWNIPMGLLYNK | 789.4 | 173.1 | 1162.6 |

Blood Sample Preparation

Blood samples were collected into EDTA coated collection tubes and centrifuged for 20 minutes at 2500 g and plasma recovered. Albumin and IgG were immunodepleted using a Qproteome Albumin/IgG antibody depletion column (Qiagen, Doncaster, Vic, Australia). The depletion column was equilibrated by gravity elution of 1 mL of PBS solution (50 mM NaH2PO4, 150 mM NaCl, pH 7.2). Depletion was performed by diluting 25 μL of plasma with 75 μL of PBS solution, applying the sample to the pre-equilibrated depletion column, and inverting the column continuously on a rotary mixer for 5 min at room temperature. Protein was recovered by centrifugation of the depletion column at 500 rpm for approximately 10 seconds and washing (×2) with 100 μL of PBS solution.

Sample Preparation for Mass Spectrometry

The depleted protein sample was concentrated and buffer exchanged using a centrifugal filter with a nominal molecular weight of 5000 Da (Ultrafree-MC, Millipore). Buffer exchange was achieved by reducing the volume of the depleted sample to approximately 150 μL using the centrifugal filter device then adding 300 μL of 50 mM ammonium bicarbonate (containing 0.005% SDS). The buffer exchange procedure was repeated a further three times and the final volume adjusted to 150 μL using 50 mM ammonium bicarbonate (containing 0.005% SDS). Proteins were reduced using dithiothreitol (DTT) by adjusting the concentration of DTT to 5 mM, and incubating each sample at 56° C. for 1 hr. After cooling to room temperature, proteins were alkylated in the dark for 1 hr with iodoacetamide (IAA) at a concentration of 15 mM. Protein's were digested with trypsin (20 ug) at 37° C. for 6 hr (enzyme:substrate ratio approximately 1:25).

Liquid Chromatography and Mass Spectrometry Analysis

The digested sample (10 μL) was analysed using a 4000 QTRAP hybrid triple quadrupole/linear ion trap mass spectrometer (Applied Biosystems, Foster City, Calif., USA) operating in positive ion mode. Peptides were separated by nanoflow liquid chromatography using an Eksigent 2D LC system (Eksigent Technologies, Dublin, Calif., USA). The digested sample was analysed by injecting 10 μL of the digest onto a pre-column (Captrap 0.5×2 mm, Michrom BioResources Inc, Auburn, Calif., USA) for pre-concentration with 95:5 mobile phase A:mobile phase B (mobile phase A: 2% v/v acetonitrile containing 0.1% v/v formic acid, mobile phase B: 80% v/v acetonitrile containing 0.1% v/v formic acid) at 10 μl/min. Peptides were then separated using a ProteCol C18 column (300 Å, 3 μm, 150 μm×10 cm, SGE Analytical Sciences, Ringwood, Victoria, Australia). Peptides were eluted from the column using a linear gradient from 95:5 mobile phase A:mobile phase B to 45:55 mobile phase A:mobile phase B over 60 minutes at a flowrate of 600 nL/min. The LC eluent was subject to positive ion nanoflow analysis using a NanoSpray II source equipped with a MicroIonSpray II spray head. Column eluent was directed into the MicroIonSprayII spray head via coupling to a distal coated PicoTip fused silica spray tip (360 um OD, 75 um ID, 15 um diameter emitter orifice, New Objective, Woburn, Mass., USA). Samples were analysed using an ion spray voltage, heater interface temperature, curtain gas flow, and nebulizing gas flow of 2.1 kV, 150° C., 18, and 12, respectively. Collision energy (CE) was determined using the following equation CE=slope×(m/z)+intercept, where, slope=0.050 and intercept=5.5 for +2 precursor ions.

MS data was searched against all human entries in the SWISS-PROT database (version 53.2) using Mascot (Matrix Science, London, UK).

USRM2 Scanning:

USRM2 experiments utilised the combination of a precursor ion (Q1), and a pair of product ions (Q3a, Q3b) appropriate for each UMD. Wherever possible, these experiments utilised a primary Q3 value corresponding to the highest intensity product ion that constituted a USRM2 pair and a secondary Q3 value corresponding to the second most intense product ion that constituted the USRM2 pair for each peptide candidate. Additional USRM2s utilising UMD other than the first and second most intense product ion pairs were also assessed wherever possible. USRM2 assays were validated by triggering a product ion scan (MS/MS) when individual SRM signals exceeded 300 cps Example 4

Detection of an Entire Metabolic Pathway in a Bacterial Proteome Sample

Figure 21:
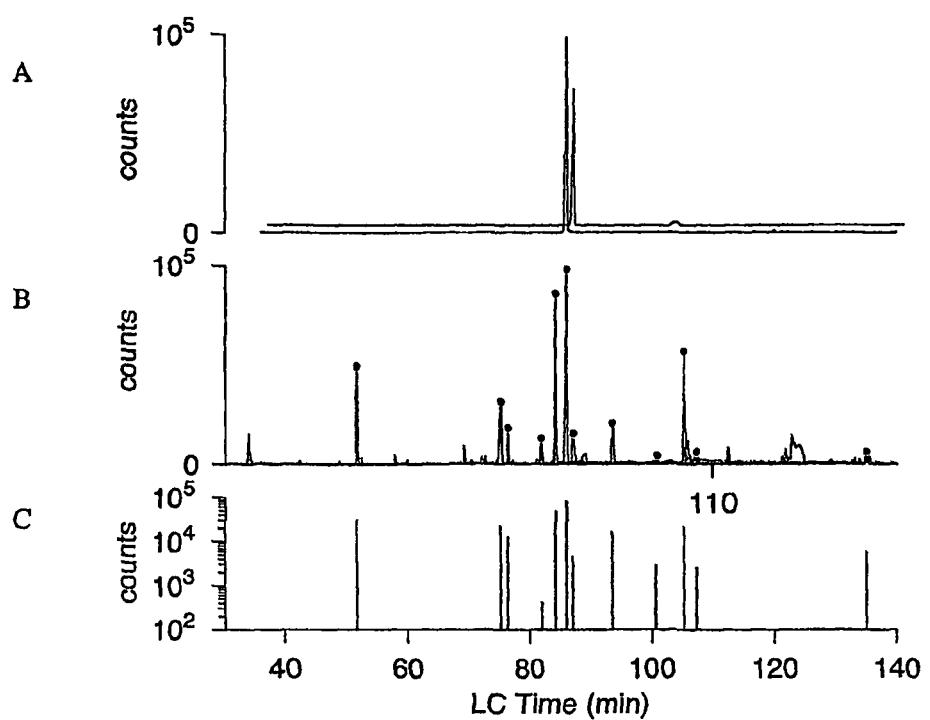
FIG. 21: USRM2 scans for E. coli TCA proteins. A) Time offset extracted ion chromatograms (XICs) for the Q3a and Q3b ions that form the UMD for the peptide GISYETATFPWAASGR from DIdH. Two independent SRM scans (ie. USRM2) were needed to address this UMD. The signals co-elute but are offset for clarity. B) Overlaid XICs from USRM2 scans for TCA peptides. XICs of the 13 identified TCA peptides (Table 3) are indicated by black dots above each peak. C) Barcode representation of the E. coli TCA obtained by USRM2 scans in B). The representation was calculated as a function of the product of Q3a and Q3b ion intensifies for each UMD. The bars in C) correspond to, and are vertically aligned in the figure with, peptides detected by USRM2 in B).

The broad applicability of the method of the present invention (uSRM) for targeted proteome profiling was demonstrated by analysing proteins of the *E. coli* tricarboxylic acid cycle (TCA). The UMD were calculated for peptides from 13 TCA enzymes representing each metabolic step of the cycle as shown in Table 3. *E. coli* cells were lysed, digested with trypsin, prepared for MS analysis and injected into the MS. USRM2 assays utilising Q1, and Q3a, Q3b values from the UMD calculation were used to configure the MS and detect each of the 13 enzymes in sequential MS runs (FIG. 8-20). In 11 of 13 peptides, tandem MS and database matching was used to confirm the identity of each peptide. The preceding data was used to select optimised USRM2 assays for each of the 13 peptides (Table 3). The MS was configured with this data to detect each of the 13 peptides in a single MS run (FIG. 21).

Methods

Calculation of Unique Mass Descriptors (UMD):

The *E. coli* proteome was downloaded from SWISS-PROT release 51.6. A set of variables was used for the calculation that included: the order of the USRMs (one Q1 and two Q3 values), use of trypsin for proteolysis, the number of possible missed cleavage sites set at 2, possible modifications of certain amino acids (oxidation of methionine and reduction of cysteine), the number of allowed charge states (+1, +2, +3), and the number of heavy isotopes to consider (+1, . . . +5 amu). Using this description all the possible peptides were generated, X was substituted for isoleucine and leucine, and the peptides then mapped into a set. If the peptide being loaded was already present in the set it was marked as redundant and excluded as a candidate having a UMD. From this set the peptides that contain no inappropriate cleavage residues and are non-redundant in the proteome and fall within a 300-2000 m/z domain were candidates for potential UMD addresses. For each candidate peptide, all charged peptides within a given tolerance (e.g. +/−1 m/z) were pooled. From the pooled peptides, the candidate peptide's fragment ions were generated (i ions), and all the possible combinations of Q3 m/z were considered. For a USRMr (r=1 or 2) the number of candidate addresses is given by (i choose r)=i!/((r!)(i−r)!). These candidates were then challenged with all the combinations of fragment ions for each of the peptides in the pool. Non unique peptides were removed by determining if all Q3 values in a combination have a counterpart challenge combination where the ions are within a tolerance (e.g. +/−1 m/z) of a candidate combination. All remaining peptide fragments were considered unique and comprise a unique mass descriptor (UMD) consisting of a Q1 value and two Q3 values.

TABLE 3

USRM2 assays used for the detection 13 proteins of the *E. coli* tricaboxylic acid cycle. (NA*) Indicates no MS/MS scan was triggered during the USRM2 LC/MS/MS analysis preventing independent confirmation for the detection of these peptides.

| UniProtKB/ Swiss-Prot Entry (Gene) | Protein Name | Peptide | USRM2 Q1 | (Q3a, Q3b) | Peptide Confirmed By MS/MS (MOWSE SCORE) |
|---|---|---|---|---|---|
| ACON2_ECOLI (acnB) | Aconitate hydratase 2 | DLVHAIPLYAIK | 676.90 676.90 | 704.43, 1025.61 888.55, 1025.61 | Yes (37) |
| CISY_ECOLI (gltA) | Citrate synthase | AMGIPSSMFTVIFAMAR | 915.45 915.45 | 1055.57, 1570.81 595.30, 1360.67 | Yes (75) |
| DHSA_ECOLI (sdhA) | Succinate dehydrogenase flavoprotein subunit | LPGILELSR | 499.30 499.30 | 617.36, 787.47 375.23, 787.47 | Yes (41) |
| DHSB_ECOLI (sdhB) | Succinate dehydrogenase iron-sulfur subunit | LDGLSDAFSVFR | 663.83 663.83 663.83 | 726.39, 1213.58 508.29, 1098.56 508.29, 1041.53 | Yes (55) |
| DLDH_ECOLI (lpd) | Dihydrolipoyl dehdrogenase | GISYETATFPWAASGR | 857.41 | 1063.53, 1293.62 | Yes (65) |
| FUMA_ECOLI (fumA) | Fumarate hydratase class I, aerobic | VAPEALTLLAR | 577.35 577.35 | 886.53, 983.59 886.53, 1054.62 | Yes (33) |
| IDH_ECOLI (icd) | Isocitrate dehydrogenase [NADP] | GPLTTPVGGGIR | 562.82 562.82 562.82 | 655.37, 857.48 655.39, 970.57 756.43, 970.57 | Yes (56) |
| MDH_ECOLI (mdh) | Malate dehydrogenase | VAVLGAAGGIGQALALLLK | 868.04 868.04 | 926.60, 1352.82 926.60, 1564.98 | Yes (63) |

TABLE 3-continued

USRM2 assays used for the detection 13 proteins of the *E. coli* tricaboxylic acid cycle. (NA*) Indicates no MS/MS scan was triggered during the USRM2 LC/MS/MS analysis preventing independent confirmation for the detection of these peptides.

| UniProtKB/Swiss-Prot Entry (Gene) | Protein Name | Peptide | USRM2 Q1 | (Q3a, Q3b) | Peptide Confirmed By MS/MS (MOWSE SCORE) |
|---|---|---|---|---|---|
| | | | 868.04 | 1153.73, 1295.80 | |
| | | | 868.04 | 1153.73, 1564.98 | |
| | | | 868.04 | 670.48, 1295.80 | |
| | | | 868.04 | 670.48, 1465.91 | |
| MQO_ECOLI (mqo) | Malate:quinone oxidoreductase | VVLFGPFATFSTK | 707.39 | 482.26, 1102.55 | Yes (56) |
| | | | 707.39 | 482.26, 1215.64 | |
| ODO1_ECOLI (sucA) | 2-oxogultarate dehydrogenase E1 component | VATLEDATEMVNLYR | 862.93 | 565.31, 1340.61 | Yes (78) |
| SUCC_ECOLI (sucC) | Succinyl-CoA synthetase beta chain | AVLVNIFGGIVR | 629.38 | 648.38, 1087.66 | Yes (34) |
| | | | 629.38 | 501.31, 1087.66 | |
| ACON1_ECOLI (acnA) | Aconitate hydratase 1 | VLLENLLR | 485.30 | 515.33, 870.54 | N/A* |
| SUCD_ECOLI (sucD) | Succincyl-CoA ligase [ADP-forming] subunit alpha | SGTLTYEAVK | 534.78 | 317.22, 981.52 | N/A* |

Cell Culture:

*E. coli* K-12 (MG1655) was grown in LB media to mid log phase ($A_{600}$=1.2) and collected by centrifugation. The cells were washed with 50 mM Tris/HCl, pH 8.0, then resuspended in 50 mM ammonium bicarbonate, pH 8.5 and supplemented with protease inhibitors. The cells were lysed using a French press operated at 12000 psi, then the supernatant collected following centrifugation at 2000×g.

Sample Preparation:

1 mL of the *E. coli* lysate was adjusted to 8 M urea in 50 mM ammonium bicarbonate (pH 8.5) and reduced with TCEP (5 mM) at room temperature for 1 hour. Proteins were alkylated in 10 mM IAA for 1 hour in the dark. The sample was diluted 1:10 with 50 mM ammonium bicarbonate then digested with trypsin (20 μg) at 37° C. for 18 hours. The digest was concentrated and desalted using a 1 mL SPE cartridge. Peptides were gravity loaded onto a pre-equilibrated cartridge, desalted with 5 mL of 0.1% TFA, then eluted with 5 mL of 80% acetonitrile (0.1% TFA). Acetonitrile was removed by centrifugal evaporation to reduce the volume of the eluent to approximately 0.5 mL.

Liquid Chromatography and Mass Spectrometry Analysis:

Digested protein samples were analysed using a 4000 QTRAP hybrid triple quadrupole/linear ion trap mass spectrometer (Applied Biosystems, Foster City, Calif., USA) operating in positive ion mode. Peptides were separated by nanoflow liquid chromatography using an Eksigent 2D LC system (Eksigent Technologies, Dublin, Calif., USA). Digested samples were analysed by injecting 10 μL of the digest onto a precolumn (Captrap 0.5×2 mm, Michrom BioResources Inc, Auburn, Calif., USA) for preconcentration with 95:5 mobile phase A:mobile phase B (mobile phase A: 2% v/v acetonitrile containing 0.1% v/v formic acid, mobile phase B: 80% v/v acetonitrile containing 0.1% v/v formic acid) at 10 ul/min. Peptides were then separated using a ProteCol C18 column (300 Å, 3 μm, 150 μm×10 cm, SGE Analytical Sciences, Ringwood, Victoria, Australia). Peptides were eluted from the column using a linear gradient from 95:5 mobile phase A:mobile phase B to 45:55 mobile phase A:mobile phase B over 120 minutes at a flowrate of 600 nL/min. The LC eluent was subject to positive ion nanoflow analysis using a NanoSpray II source equipped with a MicroIonSpray II spray head. Column eluent was directed into the MicroIonSprayII spray head via coupling to a distal coated PicoTip fused, silica spray tip (360 μm OD, 75 μm ID, 15 μm diameter emitter orifice, New Objective, Woburn, Mass., USA). Samples were analysed using an ion spray voltage, heater interface temperature, curtain gas flow, and nebulizing gas flow of 2.1 kV, 150° C., 18, and 12, respectively. USRM2 experiments conducted for each protein in the TCA cycle used unit resolution settings for Q1 and Q3. Collision energy (CE) was determined using the following equation CE=slope×(m/z)+intercept, where, slope=0.050 and intercept=5.5 for +2 precursor ions. MS data was searched against all *E. coli* entries in the SWISS-PROT database (version 53.2) using Mascot (Matrix Science, London, UK) and allowed for one missed cleavage, alkylation of cysteine (IAA) and oxidation of methionine.

USRM2 Scanning:

USRM2 experiments utilised the combination of a precursor ion (Q1), and a pair of product ions (Q3a, Q3b) appropriate for each UMD. Wherever possible, USRM2 experiments utilised a primary Q3 value corresponding to the highest intensity product ion that constituted a USRM2 pair and a secondary Q3 value corresponding to the second most intense product ion that constituted the USRM2 pair for each peptide candidate. Additional USRM2s utilising UMD other than the first and second most intense product ion pairs were also assessed wherever possible. USRM2 assays were validated by triggering a product ion scan (MS/MS) when individual SRM signals exceeded 300 cps.

Example 5

An Apparatus for Configuring the Mass Scan of a Mass Spectrometer

A mass spectrometer, such as a triple quadrupole mass spectrometer is configured by configuring means of an apparatus according to the invention including a processor, such as a microprocessor containing a code that requires input values to specify the uSRMs that have been pre-calculated for the target polypeptide.

Input values can be manually entered by means of an input means such as a keyboard or alternative mechanism such as a bar code reader using a unique bar code for each target polypeptide. As a minimum, a Q1 value will be input by an instrument operator. In some cases, a Q1 value and a Q3 value is required or a Q1 value and multiple Q3 values will be specified.

The microprocessor will enable initiation of an MS scan and record a signal representative of sample abundance only when ions are detected that correspond to the pre-specified Q1 and Q3 input values. In cases where USRMn is required, ie where there are "n" Q3 values, the microprocessor will instruct the MS to conduct "n" scans. The primary scan utilizes the Q1 value and the first of several Q3 values.

When ions are detected that satisfy the Q1 and first Q3 value, the microprocessor will instruct the MS to conduct "n" secondary scans using the Q1 value and "n" Q3 values. When ions are detected in these secondary scans that satisfy the Q1 value and each of the required Q3 values, the microprocessor will instruct the MS to record a signal that integrates the Q3 ion intensities from each scan. The integrated signal indicates the presence and quantity of the target polypeptide and the microprocessor reports this information to the operator.

Preferably the apparatus is adapted use with a triple quadrupole mass spectrometer.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method for testing whether a target polypeptide is present in a sample of a set of polypeptides comprising:
    a) providing a sample of a set of polypeptides to be tested for the presence of a target polypeptide;
    b) selecting a database corresponding to the set of polypeptides having information stored therein that describes a characteristic of each polypeptide of the set, wherein the database is created according to the following steps comprising:
        i) selecting a first database having information representing amino acid sequences of substantially all polypeptides of a set of polypeptides stored therein;
        ii) utilizing each sequence to predict a mass/charge ratio for each polypeptide of the set of polypeptides obtainable when a pre-defined ionization condition is applied to polypeptides of the set;
        iii) selecting sequences that represent polypeptides that have the same predicted mass/charge ratio;
        iv) predicting a mass of each fragment ion obtainable from polypeptides represented by each selected sequence when a pre-defined fragmentation condition is applied to each polypeptide represented by the selected sequences;
        v) for each polypeptide represented by the selected sequences, identifying a predicted mass of at least one fragment ion that is different from the predicted masses of fragment ions of polypeptides represented by other selected sequences, to derive one or more values for each polypeptide of the set of polypeptides that distinguishes polypeptides of the set from each other;
        vi) storing each value so derived in a computer readable medium, thereby creating the database containing values for distinguishing each polypeptide of a set of polypeptides from each other;
    c) interrogating the database to determine a value for the target polypeptide that can be used to configure a mass spectrometer to exclude the detection of polypeptides having a value that is not the same as the value determined for the target polypeptide, so that the target polypeptide may be selectively detected by the mass spectrometer;
    d) utilizing the value determined for the target polypeptide to configure the mass spectrometer;
    e) applying the sample of the set of polypeptides to the configured mass spectrometer; and
    f) utilizing the configured mass spectrometer to test whether the target polypeptide is present in the sample of the set of polypeptides.

2. A method for deriving one or more values for distinguishing polypeptides of a set of polypeptides from each other comprising:
    a) selecting a database having information representing amino acid sequences of substantially all polypeptides of a set of polypeptides stored therein;
    b) utilizing each sequence to predict a mass/charge ratio for each polypeptide of the set of polypeptides obtainable when a pre-defined sample ionisation condition is applied to polypeptides of the set;
    c) selecting sequences that represent polypeptides that have the same predicted mass/charge ratio;
    d) predicting a mass of each fragment ion obtainable from polypeptides represented by each selected sequence when a pre-defined fragmentation condition is applied to each polypeptide represented by the selected sequences;
    e) for each polypeptide represented by the selected sequences, identifying a predicted mass of at least one fragment ion that is different from the predicted masses of fragment ions of polypeptides represented by other selected sequences;
thereby deriving one or more values for each polypeptide of the set of polypeptides that distinguishes polypeptides of the set from each other.

3. A database containing one or more values for distinguishing each polypeptide of a set of polypeptides from each other, wherein the database is created according to the following steps comprising:
   a) selecting a first database having information representing amino acid sequences of substantially all polypeptides of a set of polypeptides stored therein;
   b) utilizing each sequence to predict a mass/charge ratio for each polypeptide of the set of polypeptides obtainable when a pre-defined ionization condition is applied to polypeptides of the set;
   c) selecting sequences that represent polypeptides that have the same predicted mass/charge ratio;
   d) predicting a mass of each fragment ion obtainable from polypeptides represented by each selected sequence when a pre-defined fragmentation condition is applied to each polypeptide represented by the selected sequences;
   e) for each polypeptide represented by the selected sequences, identifying a predicted mass of at least one fragment ion that is different from the predicted masses of fragment ions of polypeptides represented by other selected sequences, to derive one or more values for each polypeptide of the set of polypeptides that distinguishes polypeptides of the set from each other;
   f) storing each value so derived in a computer readable medium, thereby creating the database containing values for distinguishing each polypeptide of a set of polypeptides from each other.

4. An apparatus for configuring a mass scan of a mass spectrometer to test whether a target polypeptide of a set of polypeptides is present in a sample of the set comprising:
   a) a processor having stored thereon an executable code for deriving one or more values for distinguishing a target polypeptide from other polypeptides of a set of polypeptides;
   b) input means in communication with the processor for identifying the target polypeptide for which the one or more values is to be derived by the executable code;
   c) configuring means in communication with the processor for configuring a mass scan of a mass spectrometer according to the one or more values derived by the executable code; wherein in use, the executable code derives the one or more values according to the following steps:
   (i) utilizing information representing the amino acid sequences of the polypeptides of the set of polypeptides to predict a mass/charge ratio for each polypeptide obtainable when a pre-defined ionzation condition is applied to polypeptides of the set;
   (ii) selecting sequences that represent polypeptides that have the same predicted mass/charge ratio as the target polypeptide;
   (iii) predicting a mass of each fragment ion obtainable from polypeptides represented by each selected sequence when a pre-defined fragmentation condition is applied to each polypeptide represented by the selected sequences;
   (iv) identifying a predicted mass of at least one fragment ion of the target polypeptide that is different from the predicted masses of fragment ions of polypeptides represented by the selected sequences;
   thereby deriving one or more values for distinguishing the target polypeptide from other polypeptides of a set of polypeptides.

5. A method for testing whether a target polypeptide is present in a sample of a set of polypeptides comprising:
   a) providing a sample of a set of polypeptides to be tested for the presence of a target polypeptide;
   b) selecting a database corresponding to the set of polypeptides having information stored therein that describes a characteristic of each polypeptide of the set,
   c) interrogating the database to determine one or more values for the target polypeptide that can be used to configure a mass spectrometer to exclude the detection of polypeptides having a value that is not the same as the one or more values determined for the target polypeptide, so that the target polypeptide may be selectively detected by the mass spectrometer;
   d) utilizing the one or more values determined for the target polypeptide to configure the mass spectrometer;
   e) applying the sample of the set of polypeptides to the configured mass spectrometer; and
   f) utilizing the configured mass spectrometer to test whether the target polypeptide is present in the sample of the set of polypeptides,
   wherein said database is created according to the following steps comprising:
   i) selecting a first database having information representing amino acid sequences of substantially all polypeptides of a set of polypeptides stored therein;
   ii) utilizing each sequence to predict a mass/charge ratio for each polypeptide of the set of polypeptides obtainable when a pre-defined ionization condition is applied to polypeptides of the set;
   iii) selecting sequences that represent polypeptides that have the same predicted mass/charge ratio;
   iv) predicting a mass of each fragment ion obtainable from polypeptides represented by each selected sequence when a pre-defined fragmentation condition is applied to each polypeptide represented by the selected sequences;
   v) for each polypeptide represented by the selected sequences, identifying a predicted mass of at least one fragment ion that is different from the predicted masses of fragment ions of polypeptides represented by other selected sequences, to derive one or more values for each polypeptide of the set of polypeptides that distinguishes polypeptides of the set from each other.

6. A method for testing whether a target polypeptide is present in a sample of a set of polypeptides wherein said target polypeptide has one or more values that can be used to configure a mass spectrometer to exclude the detection of polypeptides having a value that is not the same as the one or more values determined for the target polypeptide, said method comprising:
   a) providing a sample of a set of polypeptides to be tested for the presence of a target polypeptide;
   b) utilizing said one or more values of said target polypeptide to configure a mass spectrometer;
   c) applying the sample of the set of polypeptides to the configured mass spectrometer; and
   d) utilizing the configured mass spectrometer to test whether the target polypeptide is present in the sample of the set of polypeptides,
   wherein said one or more values is determined according to the following steps comprising:
   i) selecting a first database having information representing amino acid sequences of substantially all polypeptides of a set of polypeptides stored therein;
   ii) utilizing each sequence to predict a mass/charge ratio for each polypeptide of the set of polypeptides obtainable when a pre-defined ionization condition is applied to polypeptides of the set;

iii) selecting sequences that represent polypeptides that have the same predicted mass/charge ratio;

iv) predicting a mass of each fragment ion obtainable from polypeptides represented by each selected sequence when a pre-defined fragmentation condition is applied to each polypeptide represented by the selected sequences;

v) for each polypeptide represented by the selected sequences, identifying a predicted mass of at least one fragment ion that is different from the predicted masses of fragment ions of polypeptides represented by other selected sequences, to derive one or more values for each polypeptide of the set of polypeptides that distinguishes polypeptides of the set from each other;

vi) storing each value so derived in a computer readable medium, thereby creating the database containing values for distinguishing each polypeptide of a set of polypeptides from each other.

7. A method for testing whether at least a first target polypeptide and/or a second target polypeptide is present in a sample of a set of polypeptides comprising:

a) providing a sample of a set of polypeptides to be tested for the presence of at least a first target polypeptide and a second target polypeptide;

b) selecting a database corresponding to the set of polypeptides having information stored therein that describes a characteristic of each polypeptide of the set, wherein the database is created according to the following steps comprising:

i) selecting a first database having information representing amino acid sequences of substantially all polypeptides of a set of polypeptides stored therein;

ii) utilizing each sequence to predict a mass/charge ratio for each polypeptide of the set of polypeptides obtainable when a pre-defined ionization condition is applied to polypeptides of the set;

iii) selecting sequences that represent polypeptides that have the same predicted mass/charge ratio;

iv) predicting a mass of each fragment ion obtainable from polypeptides represented by each selected sequence when a pre-defined fragmentation condition is applied to each polypeptide represented by the selected sequences;

v) for each polypeptide represented by the selected sequences, identifying a predicted mass of at least one fragment ion that is different from the predicted masses of fragment ions of polypeptides represented by other selected sequences, to derive one or more values for each polypeptide of the set of polypeptides that distinguishes polypeptides of the set from each other;

vi) storing each value so derived in a computer readable medium, thereby creating the database containing values for distinguishing each polypeptide of a set of polypeptides from each other;

c) interrogating the database to determine one or more values for the at least first target polypeptide and one or more values for the second target polypeptide that can be used to configure a mass spectrometer to exclude the detection of polypeptides having a value that is not the same as the one or more values determined for the at least first target polypeptide and the second target polypeptide, so that the first target polypeptide and the second target polypeptide can be selectively detected by the mass spectrometer;

d) utilizing the first value determined for the at least first target polypeptide and the second value for the second target polypeptide to configure the mass spectrometer;

e) applying the sample of the set of polypeptides to the configured mass spectrometer; and f) utilizing the configured mass spectrometer to test whether the at least first target polypeptide and/or second target polypeptide is present in the sample of the set of polypeptides.

8. A method for testing whether at least a first target polypeptide and/or a second target polypeptide is present in a sample of a set of polypeptides wherein said first target polypeptide has one or more values that can be used to configure a mass spectrometer to exclude the detection of polypeptides having a value that is not the same as the first value and one or more second value that can be used to configure a mass spectrometer to exclude the detection of polypeptides having a value that is not the same as the one or more values determined for the first target polypeptide and second target polypeptide, said method comprising:

a) providing a sample of a set of polypeptides to be tested for the presence of a first target polypeptide and second target polypeptide;

b) utilizing said one or more values of said first target polypeptide and said one or more values of said second target polypeptide to configure the mass spectrometer;

c) applying the sample of the set of polypeptides to the configured mass spectrometer; and d) utilizing the configured mass spectrometer to test whether the first target polypeptide and/or second target polypeptide is present in the sample of the set of polypeptides, wherein said one or more values is determined according to the following steps comprising:

i) selecting a first database having information representing amino acid sequences of substantially all polypeptides of a set of polypeptides stored therein;

ii) utilizing each sequence to predict a mass/charge ratio for each polypeptide of the set of polypeptides obtainable when a pre-defined ionization condition is applied to polypeptides of the set;

iii) selecting sequences that represent polypeptides that have the same predicted mass/charge ratio;

iv) predicting a mass of each fragment ion obtainable from polypeptides represented a pre-defined fragmentation condition is applied to each polypeptide represented by the selected sequences;

v) for said first polypeptide and said second polypeptide represented by the selected sequences, identifying a predicted mass of at least one fragment ion that is different from the predicted masses of fragment ions of polypeptides represented by other selected sequences and the other of said first polypeptide and said second polypeptide, to derive one or more values for said first and said second polypeptide of the set of polypeptides that distinguishes said first polypeptide and said second polypeptide of the set from each other;

vi) storing each value so derived in a computer readable medium, thereby creating the database containing values for distinguishing each polypeptide of a set of polypeptides from each other.

9. An apparatus for configuring a mass scan of a mass spectrometer to test whether one or more target polypeptides of a set of polypeptides is present in a sample of the set comprising:
   a) a processor having stored thereon one or more values for distinguishing one or more target polypeptides from the other polypeptides of a set of polypeptides;
   b) configuring means in communication with the processor for configuring a mass scan of a mass spectrometer according to the one or more values,
   wherein said one or more values is determined according to the following steps comprising:
      i) selecting a first database having information representing amino acid sequences of substantially all polypeptides of a set of polypeptides stored therein;
      ii) utilizing each sequence to predict a mass/charge ratio for each polypeptide of the set of polypeptides obtainable when a pre-defined ionization condition is applied to polypeptides of the set;
      iii) selecting sequences that represent polypeptides that have the same predicted mass/charge ratio;
      iv) predicting a mass of each fragment ion obtainable from polypeptides represented by each selected sequence when a pre-defined fragmentation condition is applied to each polypeptide represented by the selected sequences;
      v) for each polypeptide represented by the selected sequences, identifying a predicted mass of at least one fragment ion that is different from the predicted masses of fragment ions of polypeptides represented by other selected sequences, to derive one or more values for each polypeptide of the set of polypeptides that distinguishes polypeptides of the set from each other;
      vi) storing each value so derived in a computer readable medium, thereby creating the database containing values for distinguishing each polypeptide of a set of polypeptides from each other.

10. The apparatus of claim 9 wherein said configuring means are in communication with a mass spectrometer.

* * * * *